(12) United States Patent
Wang et al.

(10) Patent No.: US 11,504,427 B2
(45) Date of Patent: Nov. 22, 2022

(54) ACOUSTIC AND ULTRASOUND-BASED MECHANOGENETICS AND THERMOGENETICS FOR IMMUNOTHERAPY

(71) Applicant: The Regents of the University of California, Oakland, CA (US)

(72) Inventors: Yingxiao Wang, La Jolla, CA (US); Shu Chien, La Jolla, CA (US); Yijia Pan, La Jolla, CA (US); Yiqian Wu, La Jolla, CA (US); Shaoying Lu, La Jolla, CA (US); Kirk Shung, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 851 days.

(21) Appl. No.: 16/463,316

(22) PCT Filed: Nov. 22, 2017

(86) PCT No.: PCT/US2017/063063
§ 371 (c)(1),
(2) Date: May 22, 2019

(87) PCT Pub. No.: WO2018/098315
PCT Pub. Date: May 31, 2018

(65) Prior Publication Data
US 2020/0108145 A1    Apr. 9, 2020

Related U.S. Application Data

(60) Provisional application No. 62/425,416, filed on Nov. 22, 2016.

(51) Int. Cl.
*A61K 41/00* (2020.01)
*C07K 16/28* (2006.01)

(52) U.S. Cl.
CPC ...... *A61K 41/0033* (2013.01); *A61K 41/0028* (2013.01); *C07K 16/2803* (2013.01); *C07K 2317/569* (2013.01); *C07K 2317/622* (2013.01); *C07K 2319/03* (2013.01); *C07K 2319/33* (2013.01)

(58) Field of Classification Search
CPC .................................................. A61K 41/0033
See application file for complete search history.

(56) References Cited

U.S. PATENT DOCUMENTS

| | | | |
|---|---|---|---|
| 2002/0165191 A1* | 11/2002 | Moonen | C12N 15/86 607/108 |
| 2004/0086998 A1 | 5/2004 | Romano et al. | |
| 2016/0324989 A1 | 11/2016 | Li et al. | |
| 2019/0192691 A1* | 6/2019 | Barrett | C12N 5/0647 |

OTHER PUBLICATIONS

Carlsten et al. (Frontiers in Immunology. Jun. 2015; vol. 6, article 266, pp. 1-9; https://doi.org/10.3389/fimmu.2015.00266) (Year: 2015).*
Ede et al. (ACS Synth. Biol. 2016, 5, 395-404). (Year: 2016).*
Antigny et al. (Frontiers in Pharnacology. Oct. 2011; vol. 2; Article 67; pp. 1-8). (Year: 2011).*
Thomas, International Search Report for PCT/US2017/019435 dated Feb. 15, 2018.
Thomas, Written Opinion for PCT/US2017/019435 dated Jan. 19, 2018.

* cited by examiner

*Primary Examiner* — Scott Long
(74) *Attorney, Agent, or Firm* — Greer, Burns & Crain, Ltd.; Gregory P. Einhorn

(57) ABSTRACT

In alternative embodiments, provided are compositions, including products of manufacture and kits, and methods, for remotely-controlled and non-invasive manipulation of intracellular nucleic acid expression, genetic processes, function and activity in live cells, e.g., adding functions or changing or adding specificities for immune cells, for monitoring physiologic processes, for the correction of pathological processes and for control of therapeutic outcomes. In alternative embodiments, provided are ultrasound-based thermal or mechanical stimulations, and thermo- or mechano-sensitive protein, either synthetically engineered or natively (endogenously) occurring, integrated to control the production of intracellular nucleic acid and gene expression, e.g., for the expression of biological-active proteins, which can be used, in alternative embodiments, for diagnostic or therapeutic purposes. In alternative embodiments, exemplary thermo- and mechanogenetic systems provided herein allow a deep penetration of stimulation and manipulation in vivo at centimeter-level depth with high spatiotemporal precision.

37 Claims, 28 Drawing Sheets

ACOUSTIC AND ULTRASOUND-BASED MECHANOGENETICS AND THERMOGENETICS FOR IMMUNOTHERAPY

RELATED APPLICATIONS

This application is a national phase application claiming benefit of priority under 35 U.S.C. § 371 to Patent Cooperation Treaty (PCT) International Application Serial No: PCT/US2017/063063, filed Nov. 22, 2017, which claims the benefit of priority to U.S. Provisional Patent Application Ser. No. (USSN) 62/425,416, filed Nov. 22, 2016. The aforementioned applications are expressly incorporated herein by reference in their entirety and for all purposes.

STATEMENT AS TO FEDERALLY SPONSORED RESEARCH

This invention was made with government support under HL109142, HL098472, and HL121365 awarded by the National Institutes of Health. The government has certain rights in the invention.

TECHNICAL FIELD

This invention generally relates to thermo- and mechanogenetics, cell biology and ultrasound technologies. In alternative embodiments, provided are compositions, including products of manufacture and kits, and methods, for remotely-controlled and non-invasive manipulation of intracellular nucleic acid expression, genetic processes, function and activity in live cells, e.g., adding functions or changing or adding specificities for immune cells, for monitoring physiologic processes, for the correction of pathological processes and for the control of therapeutic outcomes. In alternative embodiments, provided are ultrasound-based mechanical stimulations and a mechanosensitive protein, e.g., a transmembrane protein or a channel or channels, either synthetically engineered or natively (endogenously) occurring, integrated to control the production of intracellular nucleic acid and gene expression, e.g., for the expression of biological-active proteins, which can be used, in alternative embodiments, for diagnostic or therapeutic purposes. In alternative embodiments, exemplary thermo- and mechanogenetic systems provided herein, being based on ultrasound and/or heat, allow a deep penetration of stimulation and manipulation in vivo at centimeter-level depth with high spatiotemporal precision.

BACKGROUND

Artificial T cell receptors (also known as chimeric T cell receptors, chimeric immunoreceptors, chimeric antigen receptors (CARs)) are engineered receptors, which graft a desired specificity onto an immune effector cell such as a T cell. CAR T cell therapy is becoming a paradigm-shifting therapeutic approach for cancer treatment, particularly with the benefit of resulted central memory T cells capable of lasting for months to years in suppressing the cancer relapse. In this therapy, T cells are removed from a cancer patient and modified to express CARs that target the cancer. These modified T cells, which can recognize and kill the patient's cancer cells, are re-introduced into the patient.

However, major challenges remain before CAR-based immunotherapy can become widely adopted. For instance, the non-specific targeting of the CAR-T cells against normal/nonmalignant tissues (on-target but off-tumor toxicities) can be life-threatening. In fact, off-tumor toxicities against the lung, gray matter in the brain, and cardiac muscles, have caused multiple cases of deaths. While synthetic biology and genetic circuits have been used in attempts to address this issue, there is an urgent need for high-precision control of CAR-T cells to confine the activation in tissue space.

In immunotherapy, the expression of engineered CAR on the cell surface enables T cells to recognize specific antigens on the target cell. This triggers T cell activation and can eventually lead to the elimination of target cells. Clinical trials involving anti-CD19 CAR T cells against B-cell malignancies have shown promising results, demonstrating the therapeutic effects of CAR T cells in cancer treatment. However, the perfusion of constitutively activated CAR T cells into patients may have lethal consequences due to the induced cytokine storm and 'on-target, off tumor' toxicity. Therefore, researchers are actively seeking control over the timing and location of the activation of the perfused CAR T cells.

While optogenetics technologies enable precise control of target space, they cannot reach deep tissues. In contrast, ultrasound can be focused to deliver mechanical energy safely and noninvasively into small volumes of tissue deep inside the body. In addition, microbubbles have been well established as ultrasound imaging contrast agents and approved by the FDA for clinical use. These microbubbles are highly responsive to ultrasound due to a large difference in acoustic impedance between the surrounding media and the gas inside the bubble. Oscillatory pressure of ultrasound waves can hence exert mechanical force on cells to which the microbubbles are physically coupled.

SUMMARY

In alternative embodiments, provided are methods for remotely-controlling and non-invasively manipulating a nucleic acid expression in a cell, or an immune cell, and optionally modifying or adding a target capability or a function to the cell, or immune cell, wherein optionally the immune cell is a T cell, a monocyte, a macrophage, a dendritic cell, a natural killer cell, wherein optionally the nucleic acid is an endogenous gene, or an exogenous nucleic acid, and optionally the exogenous nucleic acid comprises or is contained in a vector or expression cassette, and optionally the exogenous nucleic acid comprises a nucleic acid encoding (expressing) a recombinant or an artificial T cell receptor (also known as a chimeric T cell receptor, a chimeric immunoreceptor, a chimeric antigen receptor and a CAR), an antibody, a single chain antibody, or a single-domain antibody (also known as sdAb or nanobody) or an antibody fragment consisting of a single monomeric variable antibody domain, the method comprising:

(a) providing a cell, an immune cell or a plurality of cells or immune cells:

(i) expressing on the cell's extracellular surface a thermo- or mechanoresponsive protein, optionally a thermo- or mechanoresponsive transmembrane protein or channel, wherein optionally the thermo- or mechanoresponsive protein comprises MechanoSensitive channels (MS channels) such as a Piezo1 or MscL, or ThermoSensitive channels (TS channels) such as a TRPV1.

and optionally the thermoresponsive or mechanoresponsive protein is an exogenous protein or an endogenous protein, or a recombinantly engineered thermoresponsive or mechanoresponsive protein; or (ii) comprising or having contained therein a nucleic acid or gene operably linked to a mammalian or a human promoter or transcriptional activator activated by increased temperature, optionally operably linked to a heat shock protein (Hsp), optionally a 70B Hsp, promoter that can be activated by heat shock, optionally at about 43° C. (for the 70B Hsp), and optionally the exogenous nucleic acid comprises or is contained in a vector or expression cassette; or expressing on its extracellular surface the thermoresponsive or mechanoresponsive protein of (i) and comprising or having contained therein a nucleic acid or gene operably linked to a mammalian or a human promoter activated by increased temperature of (ii), and the nucleic acid is operably linked to:

(i) a promoter or transcriptional activator responsive to an intracellular response or signal transmitted or generated by excitation of the mechanoresponsive protein by ultrasound stimulation of an ultrasound-responsive microbubble, wherein optionally the intracellular response or signal transmitted comprises an intracellular calcium influx; or (ii) a mammalian or a human promoter or transcriptional activator or thermoresponsive channel activated by increased temperature, optionally operably linked to a heat shock protein (Hsp), optionally a 70B Hsp, promoter that can be activated by heat shock, at optionally about 43° C. (for the 70B Hsp);

(b) and optionally, when the cell expresses on its extracellular surface a mechanoresponsive protein, providing a microbubble, or a plurality of microbubbles, capable of responding to ultrasound or equivalent, wherein the microbubble or plurality of microbubbles are linked or attached to at least one, or two or more, proteins, small molecules or moieties capable of specifically binding to the mechanoresponsive protein on the extracellular surface of the cell, such that energy generated by ultrasound stimulation of the ultrasound-responsive microbubble, or a plurality of microbubbles is transmitted to the mechanoresponsive protein to activate the mechanoresponsive protein, wherein activation of the mechanoresponsive protein causes the mechanoresponsive protein to transmit or generate an intracellular response or signal, wherein optionally the intracellular response or signal comprises a calcium influx into the cell;

(c) stimulating the cell with heat (when the cell comprises or has contained therein a nucleic acid or gene operably linked to a mammalian or a human promoter or transcriptional activator activated by increased temperature) and/or ultrasound (when the cell expresses on its extracellular surface a mechanoresponsive protein), either optionally generated by high-intensity focused ultrasound (HIFU), thereby:

causing the thermoresponsive or mechanoresponsive protein to transmit or generate an intracellular response or signal to activate expression of the nucleic acid responsive the signal generated by excitation of the thermoresponsive or mechanoresponsive protein by ultrasound stimulation, and/or activating expression of the nucleic acid responsive the mammalian or a human promoter or transcriptional activator activated by increased temperature, thereby remotely-controlling and non-invasively upregulating expression of the nucleic acid, and optionally thereby adding a function to the cell, or immune cell, or manipulating a physiologic and/or a genetic process in the cell, or immune cell, and optionally when the upregulated nucleic acid is a nucleic acid expressing (encoding) a CAR, a single chain antibody, or a single-domain antibody (also known as sdAb or nanobody) or an antibody fragment consisting of a single monomeric variable antibody domain, thereby adding a new specificity, function or target cell to a cell, an immune cell or a T cell.

In alternative embodiments, the methods further comprises engineering into the cell or cells a vector or Gene Transducing Module (GTM) such that upon stimulating the cell with:

(a) ultrasound, thereby activating the thermoresponsive or mechanoresponsive protein, optionally a thermoresponsive or mechanoresponsive transmembrane protein or channel, to transmit or generate an intracellular response or signal, and/or (b) heat, optionally generated by high-intensity focused ultrasound (HIFU);

the nucleic acid is expressed or is optimally expressed, wherein optionally the nucleic acid encodes a protein, and optionally the protein affects cell physiology or function, or adds a new target specificity to the cell, or is expressed on the cell's surface, or is secreted from the cell, and optionally the protein comprises a chimeric antigen receptor (CAR), a single chain antibody, or a single-domain antibody (also known as sdAb or nanobody) or an antibody fragment consisting of a single monomeric variable antibody domain, wherein optionally the vector or Gene Transducing Module (GTM) contains therein or comprises:

(i) the nucleic acid operably linked to a mammalian or a human promoter or transcriptional activator activated by increased temperature, optionally operably linked to a heat shock protein (Hsp), optionally a 70B Hsp; and/or (ii) a thermoresponsive or mechanoresponsive protein-expression nucleic acid operably linked to an inducible or constitutive promoter.

In alternative embodiments of the methods, the cell is a human cell or a mammalian cell, or is a cell transplanted into a tissue, an organ, an organism or an individual, or is a non-human transgenic animal genetically engineered to contain and express the Gene Transducing Module (GTM) or vector, wherein optionally the GTM or vector comprises an exogenous thermoresponsive or mechanoresponsive protein and/or an exogenous nucleic acid operably linked to a promoter or transcriptional activator responsive to: (i) an intracellular response or signal transmitted or generated by excitation of the mechanoresponsive protein by ultrasound stimulation of an ultrasound-responsive microbubble; and/or (ii) heat.

In alternative embodiments of the methods, the microbubble, or a plurality of microbubbles are connected to or caused to be operably connected to the mechanoresponsive protein by linkage or attachment directly or indirectly to at least one, or two or more, proteins, small molecules or moieties capable of specifically binding to the mechanoresponsive protein, and optionally the at least one, or two or more, proteins, small molecules or moieties comprise a streptavidin (optionally bound to the microbubble, or a plurality of microbubbles) bound to an antibody or peptide (optionally an RGD peptide) linked to a biotin, wherein the antibody specifically binds to the mechanoresponsive protein, or the RGD peptide specifically binds to an integrin, which by binding the RGD peptide transmits the ultrasound signal to the mechanoresponsive protein, or optionally the microbubble, or a plurality of microbubbles are linked to a protein or moiety capable of specifically binding to the mechanoresponsive protein.

In alternative embodiments, provided are multiplexed systems for, or used for, remotely-controlling and non-invasively manipulating a physiologic and/or a genetic process, or adding a function or target specificity, in a cell, or an immune cell, comprising:

(a)
(i) a cell or plurality of cells used to practice a method as provided herein; or
(ii) a cell, or an immune cell, or plurality of cells or immune cells, expressing on its extracellular surface:
(1) a mechanoresponsive protein, e.g., mechanoresponsive transmembrane protein or channel, wherein optionally the mechanoresponsive protein comprises a MechanoSensitive channels (MS channels) such as a Piezo1 or MscL, and optionally the mechanoresponsive protein is an exogenous protein or an endogenous protein, or a recombinantly engineered protein,
and/or
(2) a thermoresponsive protein, e.g., thermoresponsive transmembrane protein or channel, wherein optionally the thermoresponsive protein comprises a ThermoSensitive channels (TS channels), optionally as a transient receptor potential cation channel subfamily V member 1 (TrpV1) (also known as a capsaicin receptor, or vanilliod receptor-1), and optionally the thermoresponsive protein is an exogenous protein or an endogenous protein, or a recombinantly engineered protein,
and the cell or immune cell comprises or has contained therein an exogenous nucleic acid operably linked to a promoter or transcriptional activator responsive to an intracellular response or signal transmitted or generated by excitation of the thermoresponsive or mechanoresponsive protein by ultrasound stimulation directly or of an ultrasound-responsive microbubble,
wherein optionally the nucleic acid encodes a protein, and optionally the protein affects cell physiology or function, or is expressed on the cell's surface, or is secreted from the cell, and optionally the protein comprises a chimeric antigen receptor (CAR), a single chain antibody, or a single-domain antibody (also known as sdAb or nanobody) or an antibody fragment consisting of a single monomeric variable antibody domain;
(b) and optionally, a microbubble, or a plurality of microbubbles, capable of responding to ultrasound or equivalent, wherein the microbubble or plurality of microbubbles are linked or attached to at least one, or two or more, proteins, small molecules or moieties capable of specifically binding to the mechanoresponsive protein on the extracellular surface of the cell, such that energy generated by ultrasound stimulation of the ultrasound-responsive microbubble, or a plurality of microbubbles is transmitted to the mechanoresponsive protein to activate the mechanoresponsive protein, wherein activation of the mechanoresponsive protein causes the mechanoresponsive protein to transmit or generate an intracellular response or signal, wherein optionally the intracellular response or signal comprises a calcium influx into the cell.

In alternative embodiments, provided are Uses of a multiplexed system as provided herein, for remotely-controlling and non-invasively manipulating a physiologic and/or a genetic process in a cell, or an immune cell, or adding a function or target specificity to a cell, or an immune cell, wherein optionally the cell is in a tissue or organ, or is in vivo in an individual in need thereof.

In alternative embodiments, provided are methods for the manipulation or correction of a pathological process, optionally, for eradicating a tumor or a cancer in an individual in vivo, wherein optionally the individual is a human or an animal, the method comprising:

(a) engineering ex vivo or in vivo, or providing, a cell, an immune cell, or a plurality of cells or immune cells, to display or express on the cell's extracellular surface:
(1) a mechanoresponsive protein, optionally a mechanoresponsive transmembrane protein or channel, wherein optionally the mechanoresponsive protein comprises a MechanoSensitive channels (MS channels) such as a Piezo1 or MscL, and optionally the mechanoresponsive protein is an exogenous protein or an endogenous protein, or a recombinantly engineered protein,
and/or
(2) a thermoresponsive protein, optionally a thermoresponsive transmembrane protein or channel, wherein optionally the thermoresponsive protein comprises a ThermoSensitive channels (TS channels), optionally as a transient receptor potential cation channel subfamily V member 1 (TrpV1) (also known as a capsaicin receptor, or vanilliod receptor-1), and optionally the thermoresponsive protein is an exogenous protein or an endogenous protein, or a recombinantly engineered protein,
and the cell or immune cell, or plurality of cells or immune cells, comprise or have contained therein an exogenous nucleic acid operably linked to a promoter or transcriptional activator responsive to an intracellular response or signal transmitted or generated by excitation of the thermoresponsive or mechanoresponsive protein by ultrasound stimulation directly or of an ultrasound-responsive microbubble,
wherein optionally the nucleic acid encodes a protein, and optionally the protein affects cell physiology or function, or is expressed on the cell's surface, or is secreted from the cell, and optionally the protein comprises a chimeric antigen receptor (CAR), a single chain antibody, or a single-domain antibody (also known as sdAb or nanobody) or an antibody fragment consisting of a single monomeric variable antibody domain,
and optionally when the cell or immune cell, or plurality of cells or immune cells is engineered or provided ex vivo, the cell or immune cell, or plurality of cells or immune cells is administered to an individual in need thereof,
and optionally, when the cell expresses on its extracellular surface a mechanoresponsive protein, providing a microbubble, or a plurality of microbubbles, ex vivo or in vivo, wherein the microbubble or plurality of microbubbles are capable of responding to ultrasound or equivalent, wherein the microbubble or plurality of microbubbles are linked or attached to at least one, or two or more, proteins, small molecules or moieties capable of specifically binding to the mechanoresponsive protein on the extracellular surface of the cell, such that energy generated by ultrasound stimulation of the ultrasound-responsive microbubble, or a plurality of microbubbles is transmitted to the mechanoresponsive protein to activate the mechanoresponsive protein, wherein activation of the mechanoresponsive protein causes the mechanoresponsive protein to transmit or generate an intracellular response or signal, wherein optionally the intracellular response or signal comprises a calcium influx into the cell; and
(b) stimulating the cell in vivo with heat (optionally when the cell comprises or has contained therein a nucleic acid or gene operably linked to a mammalian or a human promoter or transcriptional activator activated by increased temperature) and/or ultrasound (optionally when the cell expresses on its extracellular surface a mechanoresponsive protein), either optionally generated by high-intensity focused ultrasound (HIFU), thereby:

causing the thermoresponsive or mechanoresponsive protein to transmit or generate an intracellular response or signal to activate expression of the nucleic acid responsive the signal generated by excitation of the thermoresponsive or mechanoresponsive protein by ultrasound stimulation, and/or activating expression of the nucleic acid responsive the mammalian or a human promoter or transcriptional activator activated by increased temperature, thereby remotely-controlling and non-invasively upregulating expression of the nucleic acid, and optionally thereby adding a function to the cell, or immune cell, or plurality of cells or immune cells, or manipulating a physiologic and/or a genetic process in the cell, or immune cell, or plurality of cells or immune cells, and optionally when the upregulated nucleic acid is a nucleic acid expressing (encoding) a CAR, a single chain antibody, or a single-domain antibody (also known as sdAb or nanobody) or an antibody fragment consisting of a single monomeric variable antibody domain, thereby adding a new specificity, function or target cell to the cell, or immune cell, or plurality of cells or immune cells.

In alternative embodiments of the methods as provided herein, the cell, or immune cell, or plurality of cells or immune cells is or comprises a T cell, a monocyte, a macrophage, a dendritic cell, or a natural killer cell.

In alternative embodiments, provided are engineered cells, or immune cells, or a plurality of cells or immune cells, as engineered for use in any method or embodiment as provided herein, for use as a medicament in a remotely-controlled and non-invasive manipulation of a physiologic and/or a genetic process in a cell, or an immune cell, or for the addition of a function or a target specificity to the cell, or immune cell, or plurality of cells or immune cells, or for the manipulation or correction of a pathological process, optionally, for eradicating a tumor or a cancer in an individual in vivo.

In alternative embodiments, provided are Uses of an engineered cell, or an immune cell, or plurality of cells or immune cells, as engineered for use in any method or embodiment as provided herein, as a medicament in a remotely-controlled and non-invasive manipulation of a physiologic and/or a genetic process in a cell, or an immune cell, or for the addition of a function or a target specificity to the cell, or immune cell, or plurality of cells or immune cells, or for the manipulation or correction of a pathological process, optionally, for eradicating a tumor or a cancer in an individual in vivo.

The details of one or more exemplary embodiments as described herein are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of exemplary embodiments provided herein and are not meant to limit the scope of the invention as encompassed by the claims.

FIG. 4A schematically illustrates exemplary microbubbles coated with streptavidin that can be coupled to biotinylated RGD peptides, as discussed in detail, below.

FIG. 4B graphically illustrates the time course of calcium signaling detected by FRET biosensor upon ultrasound stimulation, with normalized ratio fluorescence resonance energy transfer (FRET)/ECFP (a fluorescent protein) as a function of time, as further discussed, below.

FIG. 4C schematically illustrates images of the cells studies in FIG. 4, i.e., representative FRET/ECFP ratio images of D3cpv calcium biosensor in HEK cells expressed with (top panels) or without (bottom panels) Piezo1 before (left column) and after (right column) ultrasound stimulation.

FIG. 5A schematically illustrates exemplary microbubbles coated with streptavidin and coupled to biotinylated RGD peptides, which are attached on integrins and hence connected to Piezo1, as further discussed, below.

FIG. 5B schematically illustrates images from a calcium FRET biosensor expressed in engineered HEK cells, which show the detection of the calcium influx into the cells when the cells are targeted by ultrasound (circles indicated by broken lines); no calcium change was observed in cells without Piezo1 (data not shown).

FIG. 5C graphically illustrates data showing the ratios of the inducible firefly luciferase and the constitutively expressed *renilla* luciferase increased upon ultrasound stimulation; where data set A-B show: 1-stage Gene Transducing Module (GTM); data se C-F show: 2-stage GTM.

FIG. 5D schematically illustrates images showing that reporter Green Fluorescent Protein (GFP) expression (lower panels) can be induced upon ionomyosin or ultrasound stimulation; the upper panels show the expression of Piezo1 fused to tdTomato.

FIG. 6A schematically illustrates the cloning of two GTMs into lentiviral vectors, and testing them in Jurkat T cells.

FIG. 6B graphically illustrates data showing calcium influx can clearly trigger the activation of the reporter gene with the one-stage GTM; FIG. 6B left image, (1), illustrates data showing that ionomycin treatment for 30 min to induce the calcium influx can clearly trigger the activation of the reporter gene with the one-stage GTM; FIG. 6B, right image, (2), illustrates data showing that a two-stage GTM to reduce leaky protein productions at the basal level also allowed the induction of reporter production upon ionomycin treatment for 30 min.

FIG. 6C schematically and graphically illustrates that ultrasound stimulation for 10 min can clearly trigger the activation of the reporter gene with two one-stage GTM; upper image schematically illustrates the exemplary cassette encoding the reporting protein mNeonGreen; and the lower image graphically illustrates the data showing relative protein expression with and without ultrasound stimulation.

FIG. 7A schematically and graphically illustrates data showing that, after integrating CD19CAR into Jurkat T cells, CD19CAR-expressing Jurkats have a higher binding capacity toward the ligand CD19-expressing B cell lymphoma tumor cell line (Toledo), as comparing to Jurkats expressing the headless CD19CAR in which the extracellular domain of CD19CAR is truncated.

FIG. 7B schematically and graphically illustrates data showing a clear activation of calcium signaling as visualized by the calcium biosensors when Toledo cells are mixed with Jurkat cells expressing CD19CAR, but not those expressing the headless CD19CAR, data graphically presented in FIG. 7B, lower panel (arrow indicates time point that "Toledo cells" were added to the Jurkat cells expressing CD19CAR).

FIG. 7C graphically illustrates data from experiments that revealed that the expression of an activation marker CD69 in Jurkat cells expressing CD19CAR can be triggered by the engagement of Toledo cells.

FIG. 8A schematically illustrates a GTM containing NFAT promoter being introduced into Jurkat cells whose surfaces were then biotinylated and coupled to streptavidin-coated microbubbles, as further discussed, below.

FIG. 8B graphically illustrates data showing that the production of CD19CAR in Jurkat cells can be stimulated by ultrasound to allow the engagement of Toledo cells, where in left panel shows relative protein expression upon CAR activation and right panel shows relative mRNA expression upon CAR activation, as further discussed, below.

FIG. 8C graphically illustrates data showing: Left panel, Representative histograms of T cell activation in Jurkat cells by quantifying the expression of cell surface protein marker CD69. Jurkat and Toledo mixtures were stained with Alexa647-conjugated anti-CD69 antibody and analyzed by flow cytometry; Right panel, The bar graphs represent CD69 up-regulation (normalized percentage of CD69 positive cells) in ultrasound-induced Jurkat cells upon Toledo cell engagement.

FIG. 11A upper panel schematically illustrates an exemplary GTM design where an Hsp promoter driving the reporter eGFP was used as the heat-sensitive GTM with a constitutively expressing mCherry serving as a normalization reference to minimize cell-cell heterogeneity; and the images on the lower panels show the heat-induced gene expression of the GTM; (Left panels): the reporter gene expression in heat shock or control groups; (middle panels): the constitutive reference mCherry expression; (right panels): DIC images of the cells.

FIG. 11B upper panel illustrates an exemplary GTM containing an Hsp promoter driving the anti-CD19 CAR and the reporter eGFP; the images on the lower panels show the heat-induced gene expression of the GTM; (Left panels): the reporter gene expression in heat shock or control groups; (right panels): DIC images of the cells.

FIG. 12A graphically illustrates representative flow cytometry data showing the expression of eGFP in Jurkat cells transduced with the Hsp promoter driven eGFP 13 hours (hr) after heat shock; Left panels: control group; Right panels: heat shock group.

FIG. 12B schematically illustrate representative images showing the expression of eGFP 18 hr after heat shock in Jurkat cells transduced with the GTM in FIG. 12A.

FIG. 12C graphically illustrates representative flow cytometry data of Jurkat cells expressing the eGFP tagged anti-CD19 CAR driven by the Hsp promoter 13 hr after heat shock; Left panel: control group; Right panel: heat shock group.

FIG. 12D schematically illustrate representative images showing the expression of eGFP 23 hr after heat shock in Jurkat cells transduced with the GTM in FIG. 12C.

FIG. 14A graphically illustrates representative flow cytometry data showing the percentage of eGFP-expressing cells in the gate of mCherry+ cell, as further discussed, below.

FIG. 14B graphically illustrates representative flow cytometry data showing the percentage of CD19CAR-expressing cells in the gate of live cells, as further discussed, below.

FIG. 15A schematically illustrates an ultrasound transducer, a half cubic inch piece of raw pork, and a thermocouple connected to a thermometer are immersed in water, as further discussed, below.

FIG. 15B graphically illustrates data showing the time course represents the temperature near the focal point measured by the embedded thermocouple in the pork.

FIG. 16A schematically illustrates the experimental setup of the ultrasound stimulation system, as further discussed, below.

FIG. 16B graphically illustrates data showing the temperature of the gel right outside the tube measured by an embedded thermocouple during ultrasound stimulation.

FIG. 16C schematically illustrates the relation of the Hsp promoter to the eGFP; and in the lower panels graphically illustrates flow cytometry data showing a drastic increase in eGFP expressing cells 20 hours (hr) after ultrasound induced heat shock in the ultrasound stimulated group as compared to the control; the dashed (green) box Rs in C represents the gated area where the cells are counted as positively expressing the reporter gene.

FIG. 16D illustrates images of corresponding microscope images of FIG. 16C: Left panels, eGFP images of the reporter gene; Right panels, DIC images of the Jurkat cells.

FIG. 17A schematically illustrates that a GTM containing NFAT promoter was introduced into Jurkat cells whose surfaces were then biotinylated and coupled to streptavidin-coated microbubbles.

FIG. 17B graphically illustrates data showing that ultrasound stimulation can induce calcium signaling, as indicated by the amount of normalized fluo-4 intensity.

FIG. 17C graphically illustrates data showing CD19CAR relative protein expression in these PBMCs without additional exogenous Piezo1 or mechano-sensors.

FIG. 17D graphically illustrates data showing the production of CD19CAR in PBMC cells can be stimulated by ultrasound to allow the engagement of Nalm6 cells, which leads to the killing effect (the "relative killing effect") on target tumor cells.

Like reference symbols in the various drawings indicate like elements.

DETAILED DESCRIPTION

Figure 1:
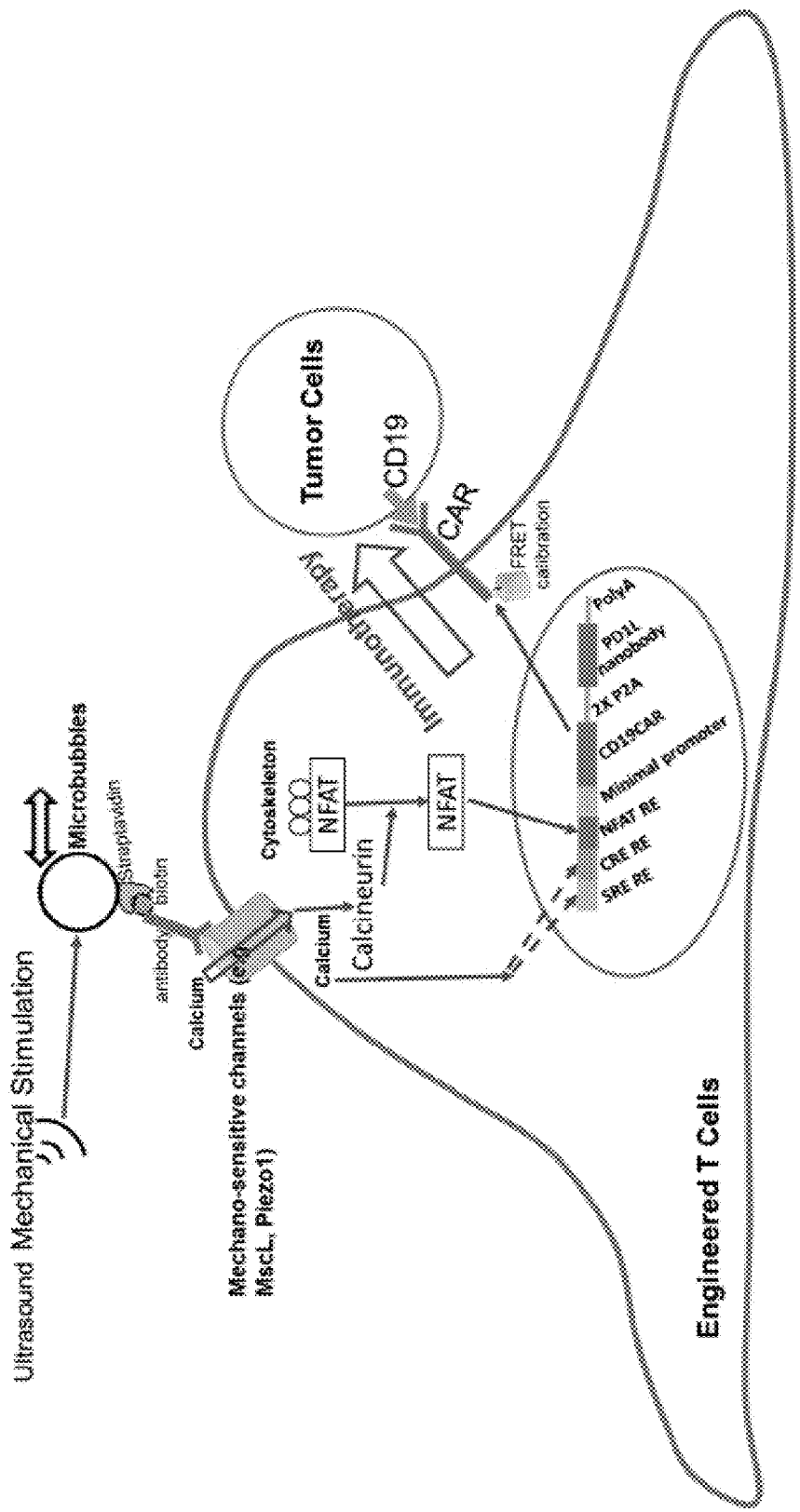
FIG. 1 schematically illustrates a diagram of an exemplary mechano-controlled immunotherapy for tumors in deep tissues in vivo, as discussed in detail, below.

In alternative embodiments, provided are compositions, including products of manufacture and kits, and methods, for remotely-controlled and non-invasive manipulation of physiologic or genetic processes and/or protein expression in live cells in vivo or ex vivo, e.g., immune cells such as T cells, for e.g., the controlled expression of recombinant nucleic acids or proteins such as e.g., chimeric T cell receptors, chimeric immunoreceptors or chimeric antigen receptors (CARs), for the manipulation of physiologic processes in the cell or for the correction of pathological processes (e.g., non-specific targeting of the CAR-T cells against normal/nonmalignant tissues) and/or for control of therapeutic outcomes, e.g., engineered T cells expressing CARs targeting specific cancers cells and killing them.

In alternative embodiments, provided are compositions and methods for the manipulation or correction of pathological processes, e.g., for eradicating tumors and cancers in human subjects, without limitation in penetration depth of an inducible signal, e.g., ultrasound stimulation. In alternative embodiment, provided are compositions and methods for inducing expression of nucleic acids, e.g., genes, in immune cells such as T cells, monocytes/macrophages, dendritic cells, natural killer cells and the like. In alternative embodiment, provided are compositions and methods for stimulating or inhibiting ligand-receptor interactions, including any surface molecular interaction, including but not limiting to inhibitory CTLA-4 and apoptotic Fas.

In alternative embodiments, provided are compositions and methods for the treatment, amelioration, prevention or eradication of a pathologic process or a pathology, a disease, an abnormal tissue, or an infection, e.g., bacterial or viral infections, with a specific cell surface marker. In alternative embodiment, provided are compositions and methods for the controlled production of RNAs (including microRNA, long non-coding RNAs), and for the epigenetic and genetic modulation of molecules for the treatment, amelioration, prevention or eradication of a pathologic process, a disease, an abnormal tissue, or an infection.

In alternative embodiments, provided are multiplexed systems comprising use of wireless devices coupling ultrasound transducers such that immunotherapy can be conducted via wireless and remote controls.

In alternative embodiments, provided are engineered immune cells, e.g., T cells, capable of inducibly expressing a recombinant protein such as a CAR, and also expressing a calcium responsive construct capable of inducibly producing or turning on the expression of the CARs, together with a mechanosensitive channel such as Piezo1. In alternative embodiments, provided are methods comprising applying ultrasound stimulation to deliver mechanical perturbation to a plurality of, or on 1 to 2, microbubbles as a mechanical amplifier, where the microbubbles are coated with streptavidin coupled with biotinylated antibody against the mechanosensitive channel on the engineered immune cells, e.g., T cells, or CARs. This exemplary system allows deep penetration in centimeters to mechanically perturb the engineered immune cells, e.g., T cells, and calcium channels, which will result in the calcium influx and turn on the gene expression of the recombinant protein, or CAR, for e.g., therapeutic, e.g., immunotherapy, activity or actions.

In alternative embodiments, biosensors based on fluorescence resonance energy transfer (FRET) are used to monitor and quantify molecular events in these engineered cells, e.g., immune cells, e.g., T cells, to serve as "digital multimeters" to allow the characterization of each molecular module for the functional optimization of the engineered cells, e.g., immune cells (immuno-cells). As such, the thermo- or mechanical energy of ultrasound can be applied to long-distance therapy, e.g., immunotherapy, in deep tissues with high resolutions in space (mm) and time.

In alternative embodiments, a similar strategy is used to control the production of nanobody against CD47 to neutralize the "don't eat me" signaling pathway of CD47 in engineered macrophages such that tumor cells with their biomarker labeled by a specific antibody can be destroyed by the phagocytosis mediated by Fcg receptors. In alternative embodiments, this approach is applied to the controlled blockage of PD-1 and CTLA-4 inhibitory signals in addition to the controlled production of CARs during a T-cell immunoresponse to promote the eradication of target tumors. Therefore, the ultrasound-based thermo- or mechano-activation provided herein can be applied to regulate long-distance gene and protein production for the controlled immunotherapy of tumors located at deep tissue regions in vivo. In alternative embodiments, ultrasound-based thermo- or mechanical stimulation, and thermo- or mechano-sensitive channels are integrated to control the production of biological-active CAR expression, which can be used, in alternative embodiments, anti-cancer therapeutic purposes. In alternative embodiments, exemplary thermogenetic or mechanogenetic systems provided herein, being based on ultrasound, allow a deep penetration of stimulation and manipulation of CAR expression in vivo at centimeter-level depth with high spatiotemporal precision.

While ultrasound has been applied to disrupt microbubbles and release anti-cancer drugs, this approach has a relatively transient effect and is limited by the microbubble targeting deficiency; and in alternative embodiments exemplary methods and systems provided herein overcome these difficulties to allow a deep penetration to control cells and enabling exemplary applications for e.g., to control the production of biological-active recombinant protein, e.g., CAR, expression.

Provided herein for the first time are compositions and methods comprising integrated use of an ultrasound-based thermo- or mechanical stimulation, and thermo- or mechano-sensitive channels to control a nucleic acid (e.g., a gene or intracellular vector or plasmid) and protein production (e.g., a CAR) for a therapy, e.g., an immunotherapy, e.g., for anti-cancer, purposes. In alternative embodiments, exemplary thermogenetic or mechanogenetic systems allow a deep penetration of stimulation and manipulation in vivo or ex vivo (as in a tissue) at centimeter levels.

While biosensors based on FRET have been broadly applied to monitor signaling transduction in cultured single cells with high spatiotemporal resolutions, also provided herein for the first time are compositions and methods comprising use of FRET biosensors monitoring immune-response signaling, which can be applied to calibrate and provide immediate feedbacks for the optimization of mechanical force-controlled or thermo-controlled gene/protein productions.

FIG. 1 schematically illustrates a diagram of an exemplary mechano-controlled immunotherapy for tumors in deep tissues in vivo. In alternative embodiments, T cells are engineered to express a mechanosensitive channel such as Piezo1 or MscL (Large Conductance Mechanosensitive Ion Channel, or MscL), as well as a calcium responsive construct capable of producing one or more chimeric antigen receptors (CARs). In alternative embodiments, an ultrasound stimulation is applied to deliver a mechanical perturbation on 1 to 2 micro microbubbles as a mechanical amplifier, where the microbubbles are coated with streptavidin to couple with biotinylated antibody against the channel (e.g., Piezo1). This exemplary system can allow the deep penetration in centimeters to mechanically perturb the engineered T cells and calcium channels, which will result in the calcium influx. This calcium signal can activate a phosphatase calcineurin to induce the transcription factor NFAT (Nuclear Factor of Activated T-cells) dephosphorylation and subsequently its nucleus translocation. The nuclear localization of NFAT, together with other calcium-sensitive transcription factors, can activate upstream promoters and turn on the gene expression of CAR for immunotherapy actions, e.g., eradication of tumor cells expressing CD19 (an exemplary target of the expressed CAR).

In alternative embodiments, biosensors based on fluorescence resonance energy transfer (FRET) are used to monitor and quantify molecular events in these cells to serve as "digital multimeters" to allow the characterization of each molecular module for the functional optimization of the engineered T cells.

Figure 2:
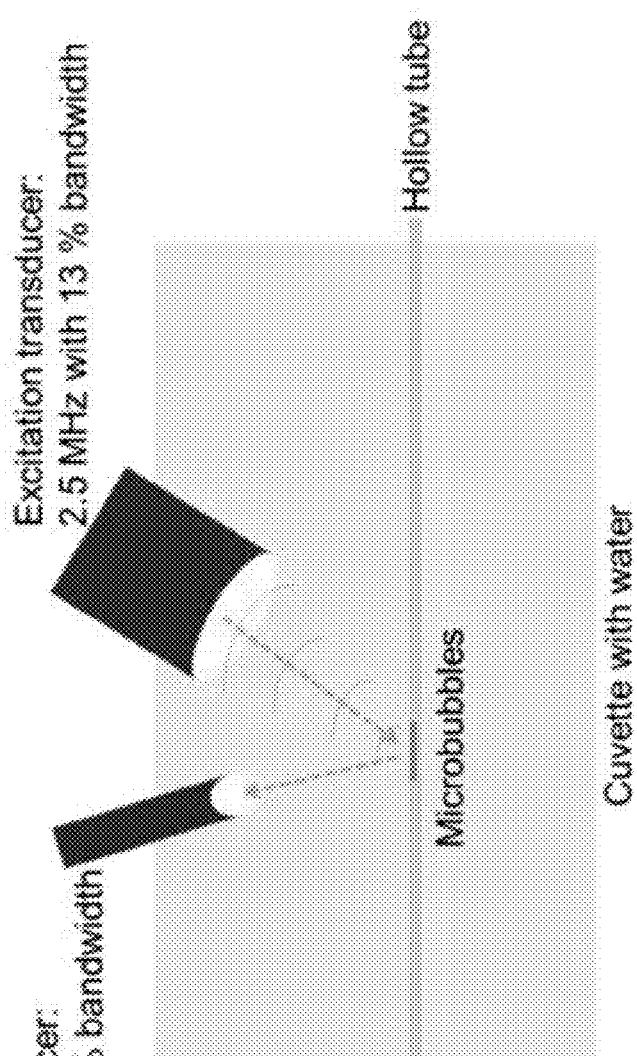
FIG. 2 schematically illustrates a diagram of an ultrasound-based mechanical stimulation and detection system as used and provided herein, as discussed in detail, below.

FIG. 2 schematically illustrates a diagram of an ultrasound-based mechanical stimulation and detection system as used and provided herein. Microbubbles were placed in a hollow tube which is submerged under water in a cuvette. An excitation ultrasound transducer can deliver a mechanical stimulation at 2.5 MHz while a receiver transducer was positioned to detect the microbubble deformation responses. The figures demonstrate an exemplary system for exciting and detecting microbubbles. Parameters were: number of cycles: 100; applied voltage: 500 mV after power amp (40 dB gain) 40V; pulse repetition frequency (PRF): 1 kHz. Receiving transducer: 10 MHz with 170% bandwidth; excitation transducer: 1.5 mHz with 13% bandwidth.

Figure 3:
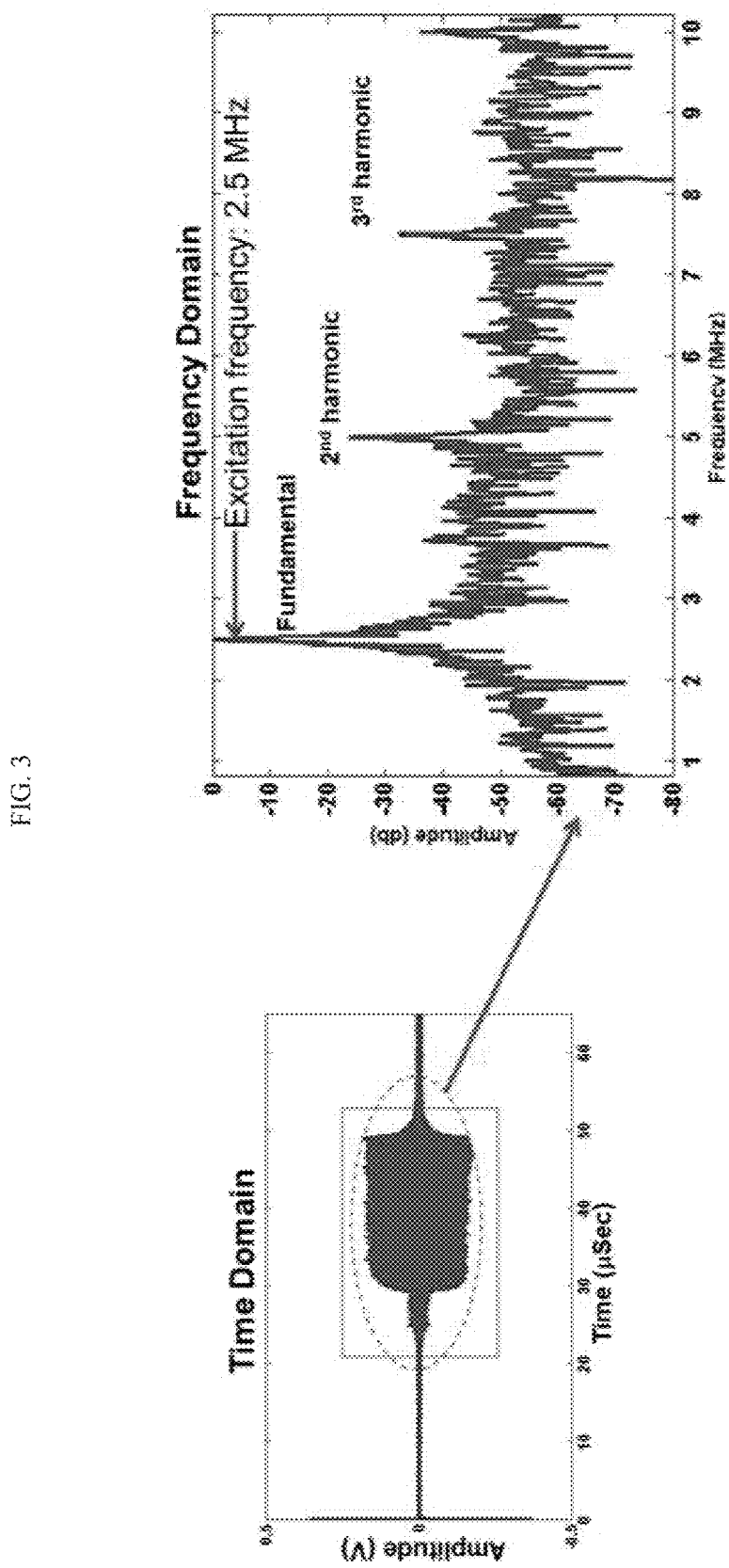
FIG. 3 schematically and graphically illustrates how microbubbles can be stimulated at a depth of 5 centimeters: Left panel, the detected microbubble responses in time domain upon ultrasound stimulation; Right panel, graphically illustrates the detected microbubble responses in frequency domain upon ultrasound stimulation.

FIG. 3 schematically and graphically illustrates how microbubbles can be stimulated at a depth of 5 centimeters. Left: the detected microbubble responses in time domain upon ultrasound stimulation; Right: graphically illustrates the detected microbubble responses in frequency domain upon ultrasound stimulation.

Figure 4A:
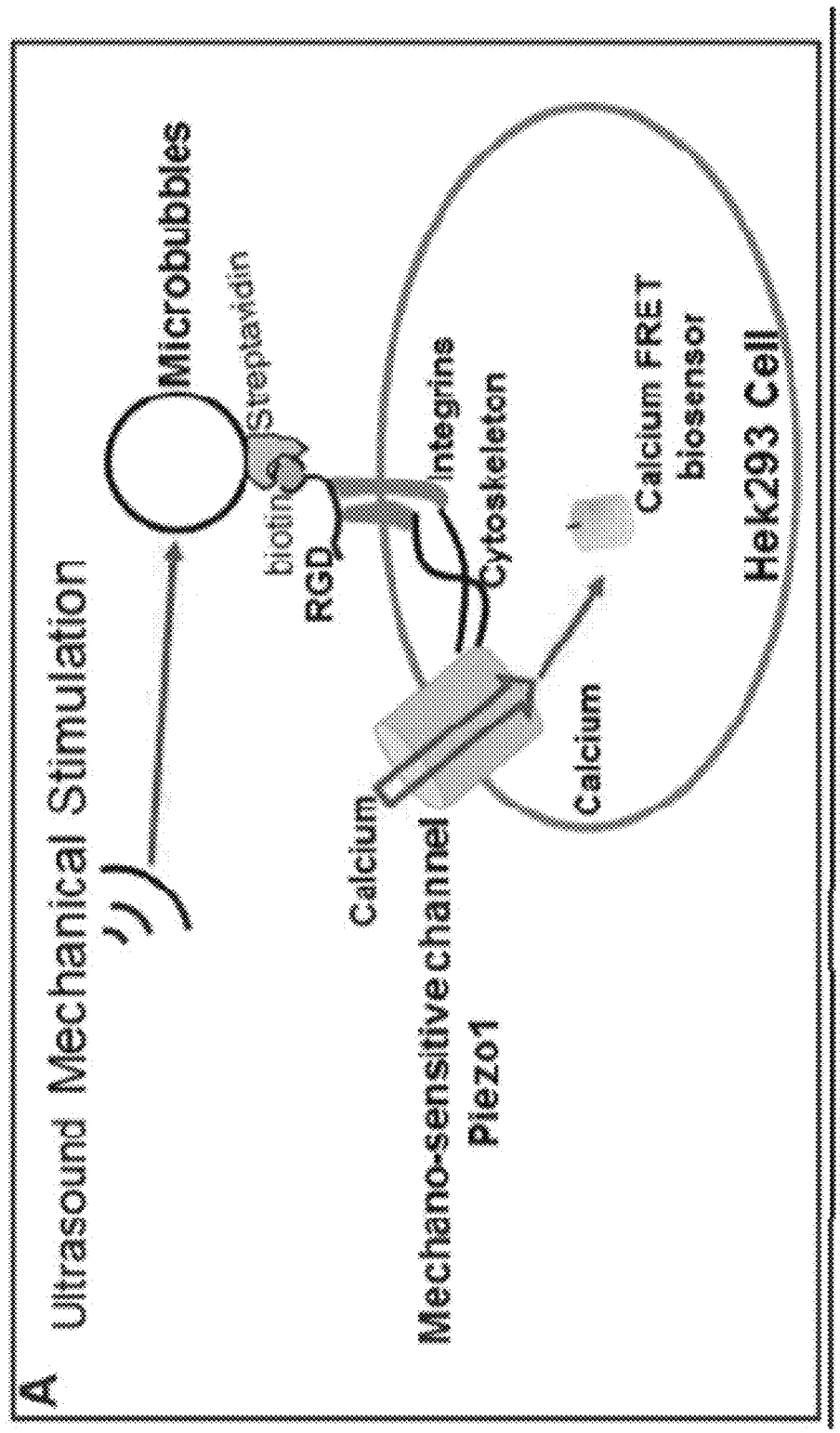
FIG. 4A-C schematically and graphically illustrate how ultrasound stimulation caused calcium response in Human Embryonic Kidney (HEK) cells expressing Piezo1 and coupled to microbubbles.
Figure 4B:
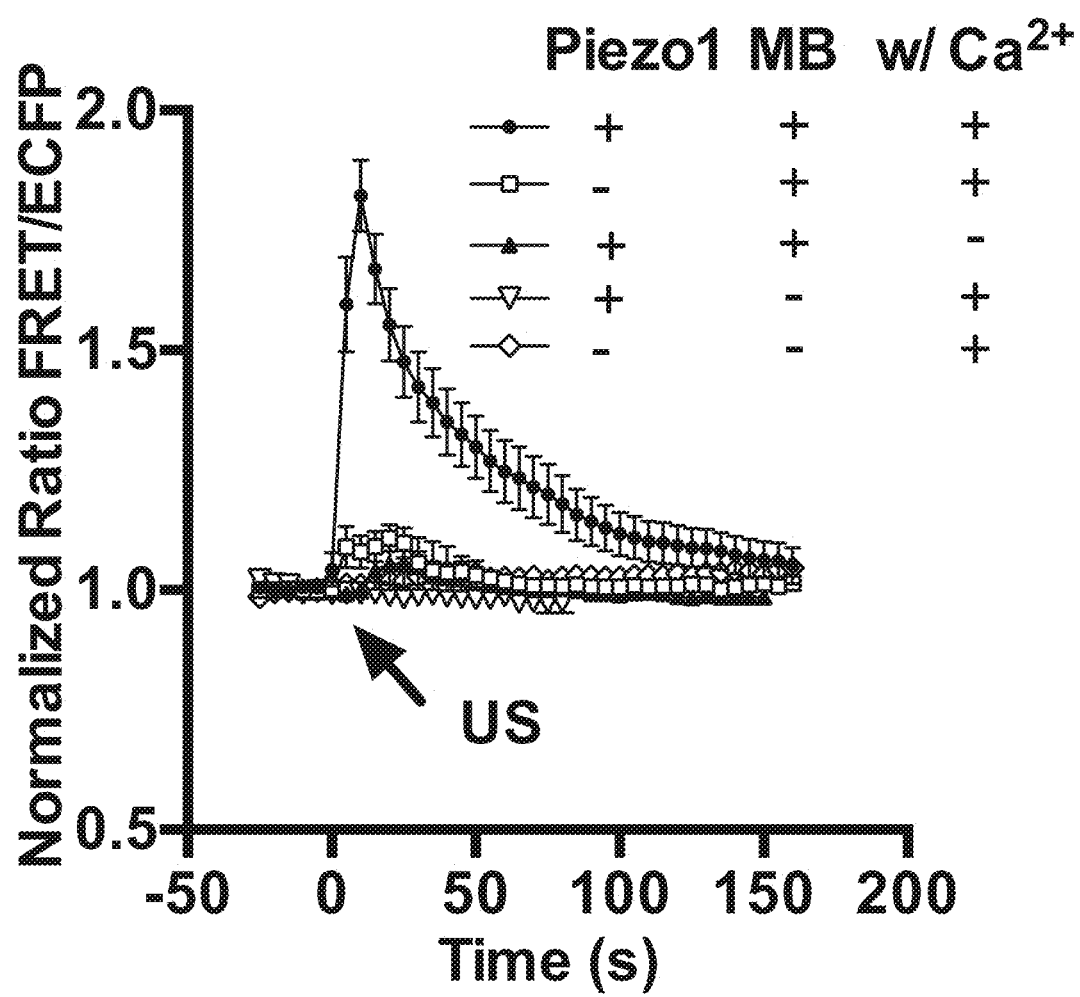
Figure 4C:
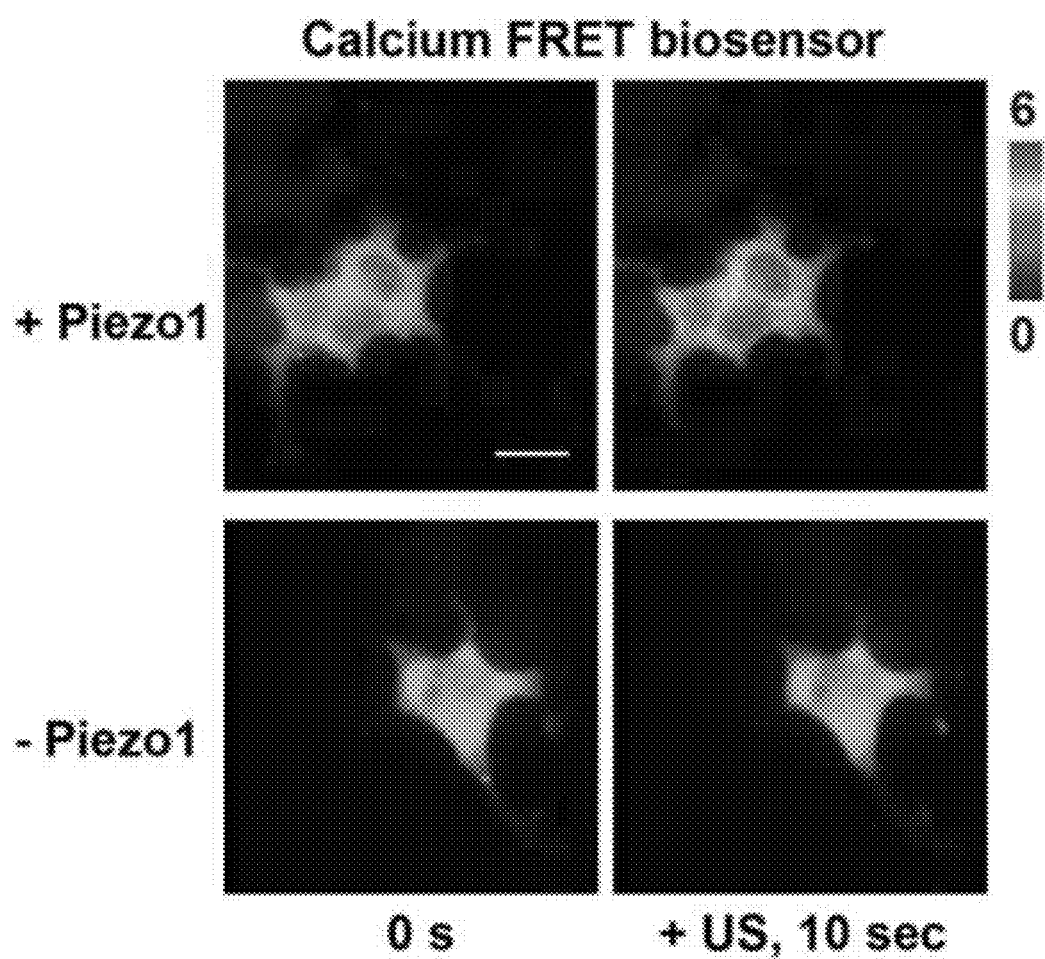

FIG. 4A-C schematically and graphically illustrate how ultrasound stimulation caused calcium response in HEK cells expressing Piezo1 and coupled to microbubbles:

FIG. 4A schematically illustrates exemplary microbubbles coated with streptavidin that can be coupled to biotinylated RGD peptides. The RGD peptides and their ligation to integrins allow the physical connection between microbubbles and mechanosensitive channel Piezo1 via cytoskeleton. It is expected that the calcium FRET biosensor expressed in HEK cells can detect the calcium influx if Piezo1 channels can be activated in long distance by the ultrasound-mediated mechanical perturbation.

FIG. 4B graphically illustrates the time course of calcium signaling detected by FRET biosensor upon ultrasound stimulation; no calcium response can be detected in HEK cells expressing Piezo1 but without microbubbles.

FIG. 4C schematically illustrates images of the cells studies in FIG. 4, i.e., representative FRET/ECFP ratio images of D3cpv calcium biosensor in HEK cells expressed with (top panels) or without (bottom panels) Piezo1 before (left column) and after (right column) ultrasound stimulation.

Figure 5A:
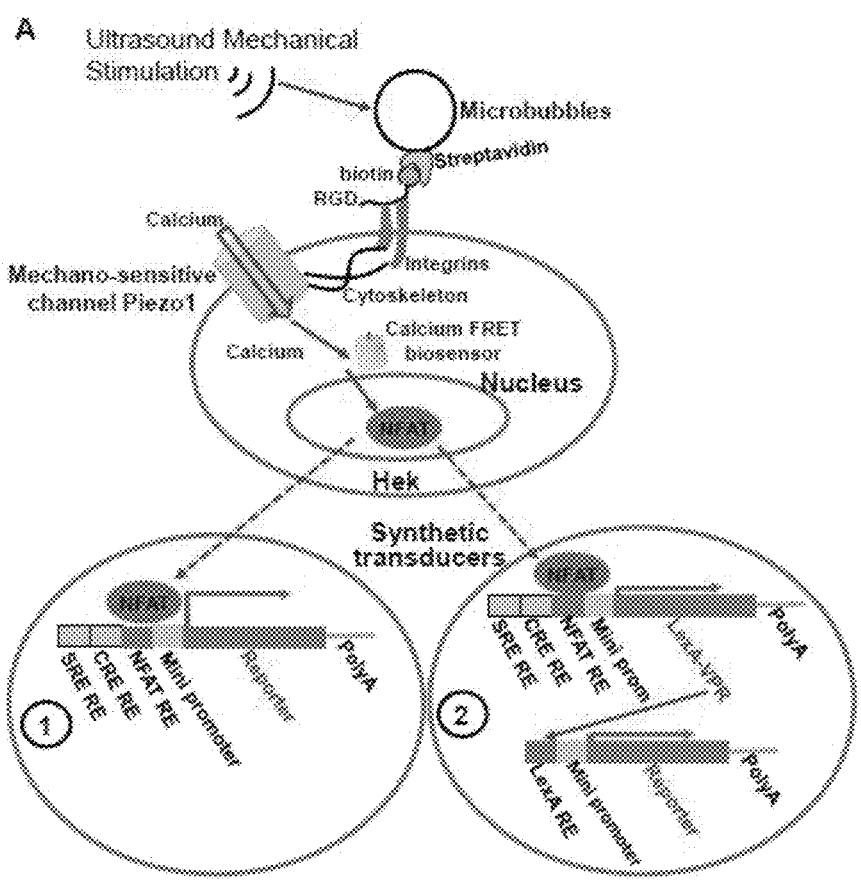
FIG. 5A-D schematically and graphically illustrate how ultrasound stimulation caused calcium and gene activations in engineered HEK cells.

FIG. 5A-D schematically and graphically illustrate how ultrasound stimulation caused calcium and gene activations in engineered HEK cells:

FIG. 5A schematically illustrates exemplary microbubbles coated with streptavidin and coupled to biotinylated RGD peptides, which are attached on integrins and hence connected to Piezo1. The ultrasound-induced calcium influx and NFAT activation can drive the reporter production via a 1-stage (left) or 2-stage (right) Gene Transducing Module (GTM). The initial product of 2-stage GTM is LexA-VPR, which can drive the final reporter production via a second gene cassette.

Figure 5B:
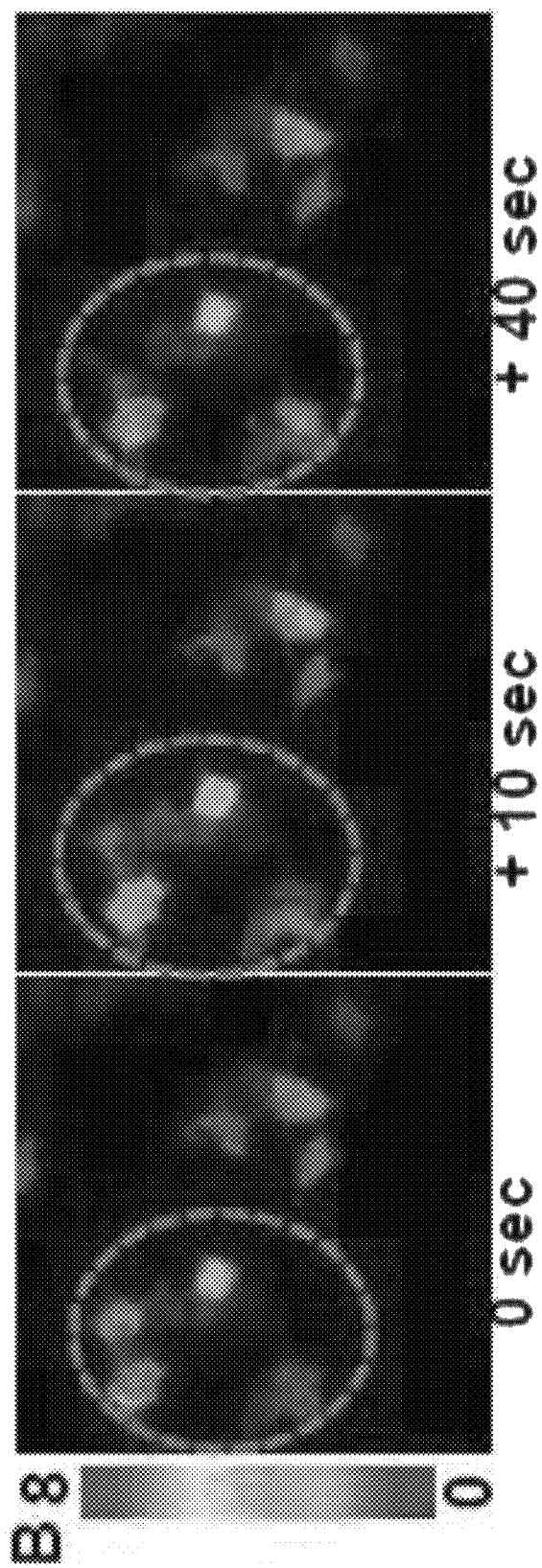

FIG. 5B schematically illustrates images from a calcium FRET biosensor expressed in engineered HEK cells, which show the detection of the calcium influx into the cells when the cells are targeted by ultrasound (circles indicated by broken lines). No calcium change was observed in cells without Piezo1 (data not shown).

Figure 5C:
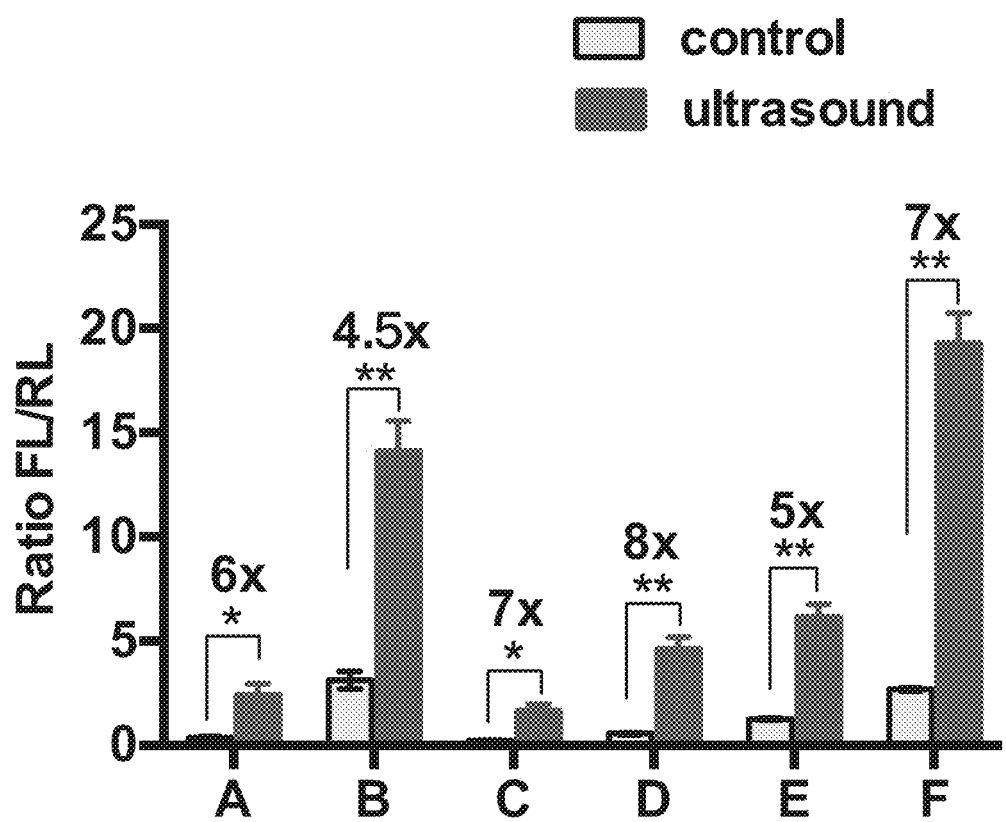

FIG. 5C graphically illustrates data showing the ratios of the inducible firefly luciferase and the constitutively expressed renilla luciferase increased upon ultrasound stimulation; where data set A-B show: 1-stage Gene Transducing Module (GTM); data se C-F show: 2-stage GTM.

Figure 5D:
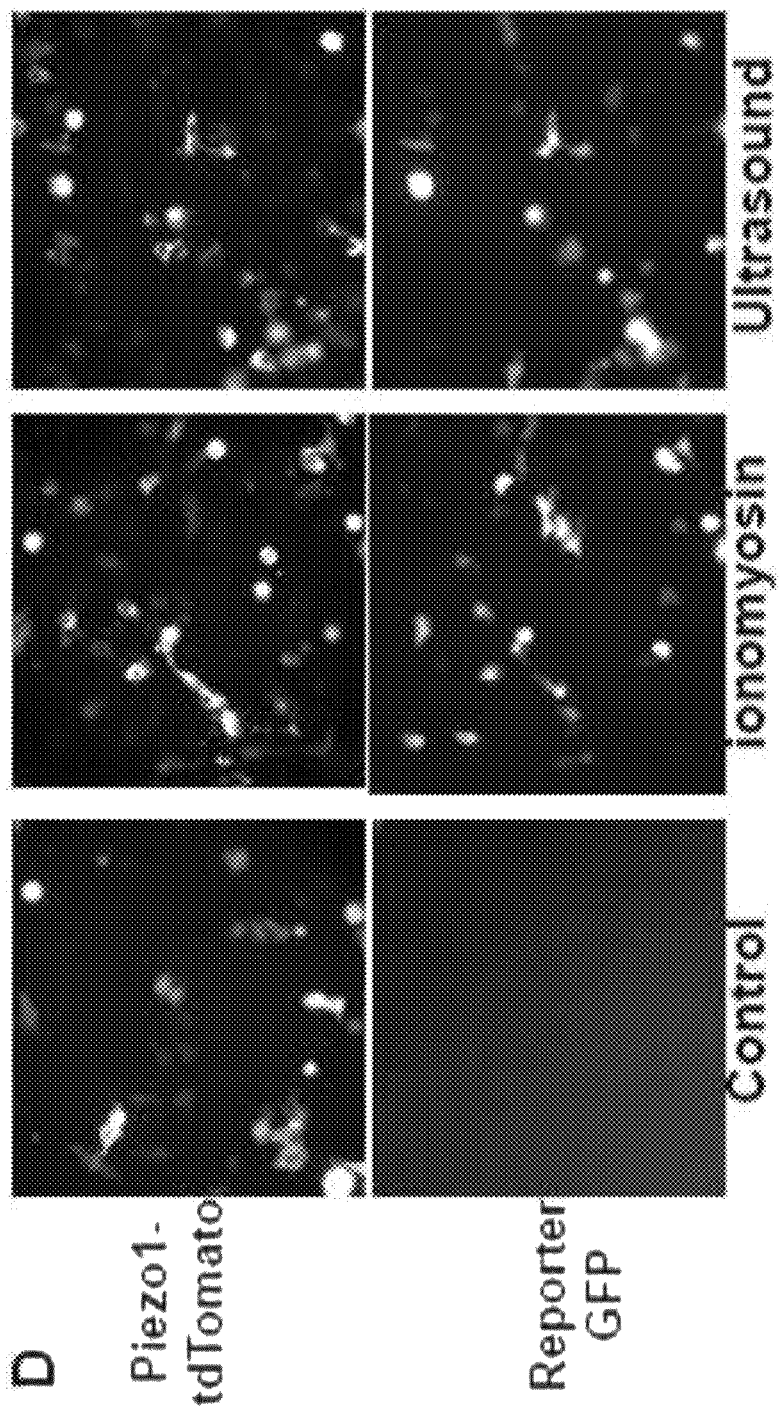

FIG. 5D schematically illustrates images showing that reporter Green Fluorescent Protein (GFP) expression (lower panels) can be induced upon ionomyosin or ultrasound stimulation. The upper panels show the expression of Piezo1 fused to tdTomato.

The Engineering and Characterization of Ultrasound-Controllable Cells.

We then examined whether it is possible to synthetically introduce mechano-sensors and gene transducing modules (GTMs) to engineer cells capable of remotely sensing ultrasound mechanical perturbation and transducing it into synthetic protein productions. Piezo1 can serve as a membrane mechano-sensor to conduct calcium influx into mammalian cells. We have established and integrated an ultrasound stimulation system with our FRET imaging microscope. We have shown that the expression of exogenous Piezo1, but not control vector, in Piezo1-deficient Hek293 cells allowed a microbubble-mediated calcium response upon 2 MHz ultrasound stimulation at a long working distance of about 5 cm (see FIG. 4A-C).

Piezo1 was then introduced as the mechano-sensor together with a GTM, in which a regulatory region composed of three calcium response elements in cis: serum response element (SRE), cyclic adenosine monophosphate response element (CRE), and the nuclear factor of activated T cell response element (NFAT RE), is placed upstream to a minimal promoter and a reporter gene (firefly luciferase, fLuc) (FIG. 5A, circle 1). The ultrasound-induced mechanical oscillation (20 min) of microbubbles coupled to integrins and hence Piezo1 clearly led to an activation in the reporter gene (FIG. 5C, samples A and B on X axis). To reduce the potentially leaky protein production in cells at the basal level and enhance the induction specificity upon stimulation, a two-stage GTM was designed (FIG. 5A, circle 2), in which the first induced protein product upon ultrasound stimulation is a DNA binding domain (DBD) LexA connected to a highly efficient transcription activator VPR (LexA-VPR). This LexA-VPR upon induction will activate a second gene cassette for the production of reporters or target proteins (FIG. 5A, circle 2). Indeed, ultrasound, similar to a chemical stimulation (ionomycin), caused a clear induction of reporter genes, either luciferase or a new GFP mNeonGreen (FIG. 5C, samples C to F as on X axis, and 5D).

The results of FIG. 5 provide the proof-of-concept that mechano-sensors and GTMs can be engineered and integrated into the endogenous molecular network for the sensing of ultrasound stimulation to guide gene activations.

Figure 6:
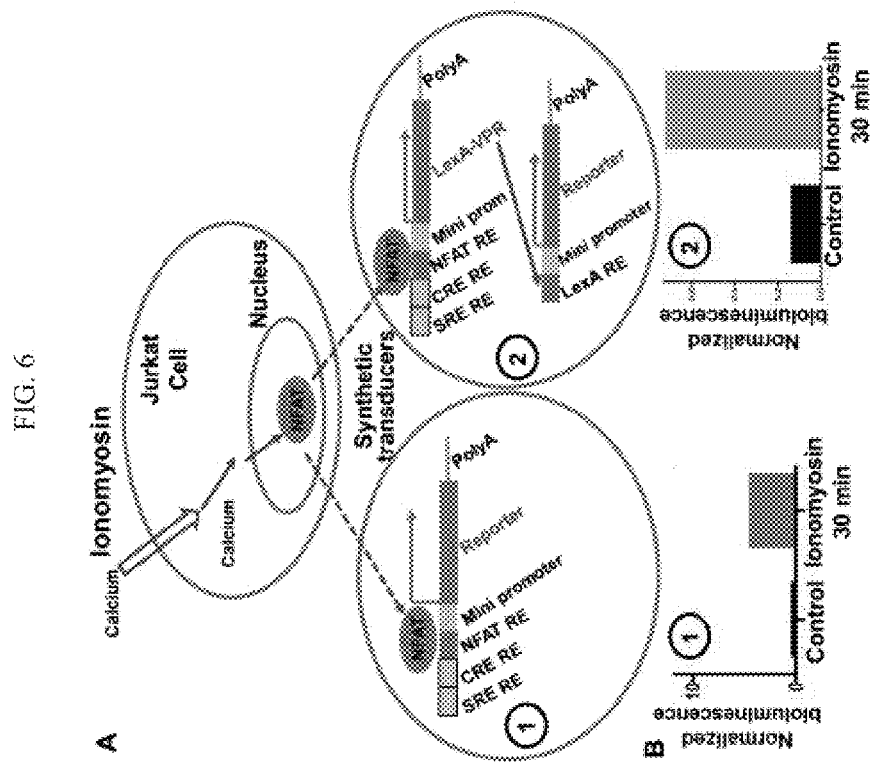
FIG. 6A-C schematically and graphically illustrate that genetic transducing modules (GTMs) are functional in T cell lines (Jurkat cells)
Figure 6C:
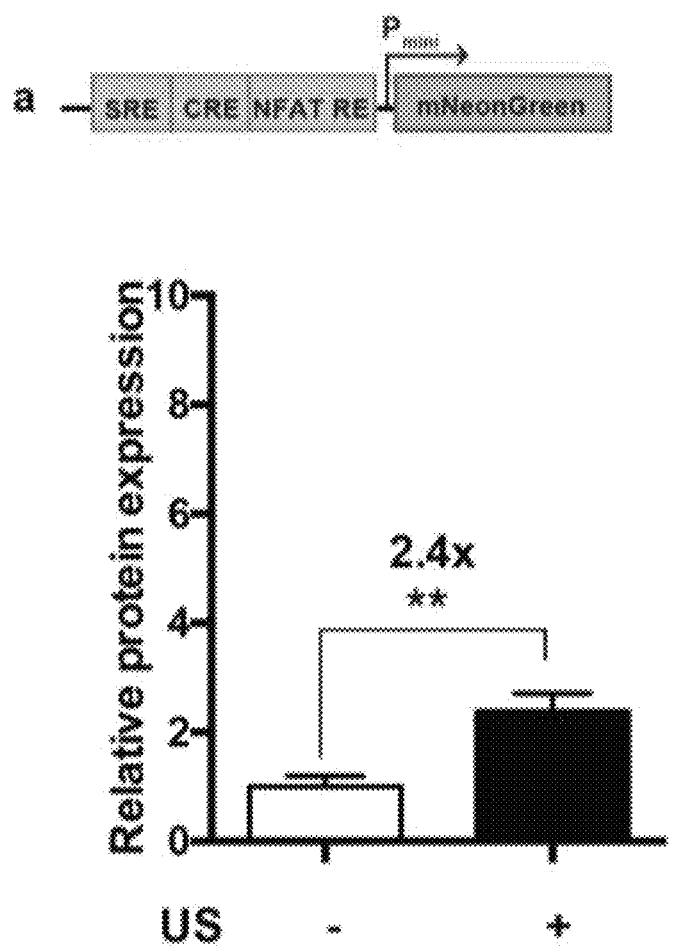

FIG. 6A-C schematically and graphically illustrate that genetic transducing modules (GTMs) are functional in T cell lines (Jurkat cells):

FIG. 6A schematically illustrates the cloning of two GTMs into lentiviral vectors, and testing them in Jurkat T cells.

FIG. 6B graphically illustrates data showing calcium influx can clearly trigger the activation of the reporter gene with the one-stage GTM; FIG. 6B left image, (1), illustrates data showing that ionomycin treatment for 30 min to induce the calcium influx can clearly trigger the activation of the reporter gene with the one-stage GTM; FIG. 6B, right image, (2), illustrates data showing that a two-stage GTM to reduce leaky protein productions at the basal level also allowed the induction of reporter production upon ionomycin treatment for 30 min.

FIG. 6C schematically and graphically illustrates that ultrasound stimulation for 10 min can clearly trigger the activation of the reporter gene with two one-stage GTM; upper image schematically illustrates the exemplary cassette encoding the reporting protein mNeonGreen; and the lower image graphically illustrates the data showing relative protein expression with and without ultrasound stimulation.

The results of FIG. 6 provide the proof-of-concept that GTMs can be integrated into the endogenous molecular network of Jurkat cells to sense the ultrasound stimulation of calcium signaling and guide gene expressions for the control of cellular functions.

Figure 7A:
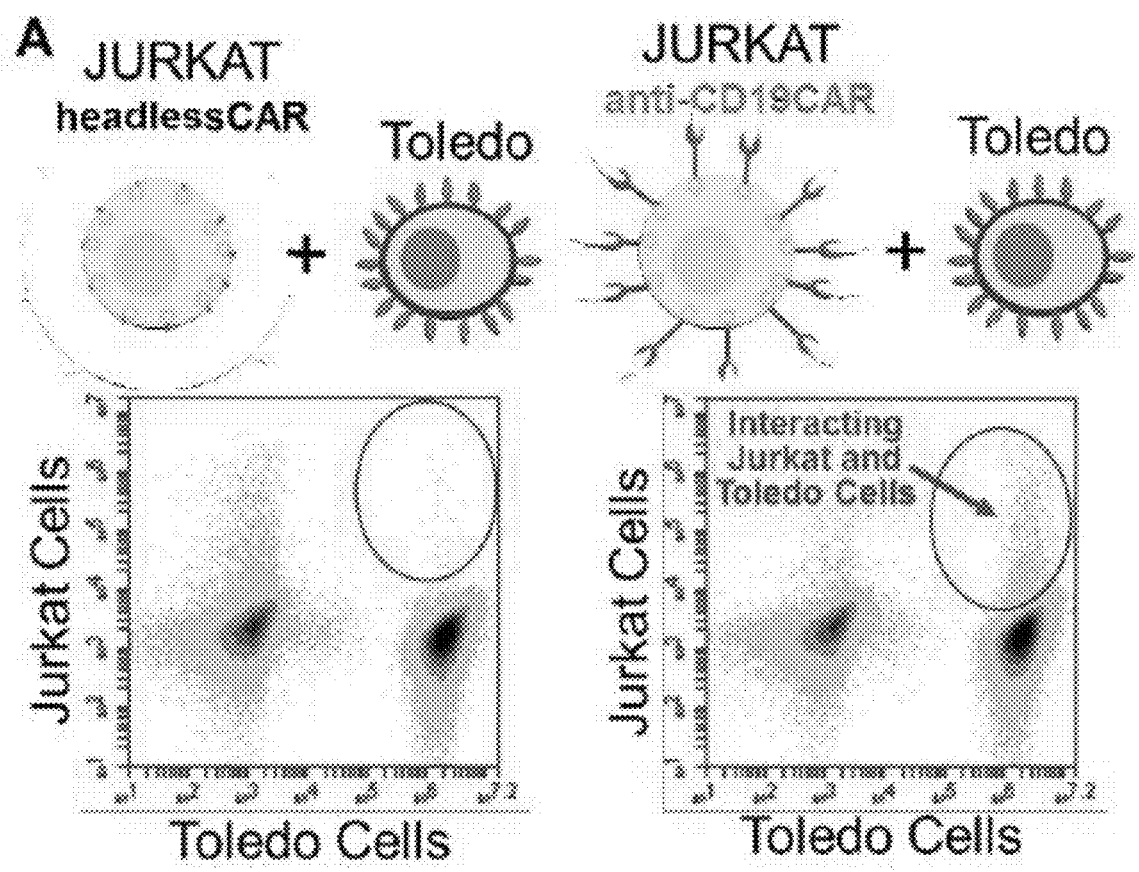
FIG. 7A-C schematically and graphically illustrate that biosensors can monitor and assess the functionality of CARs in Jurkat cells.
Figure 7B:
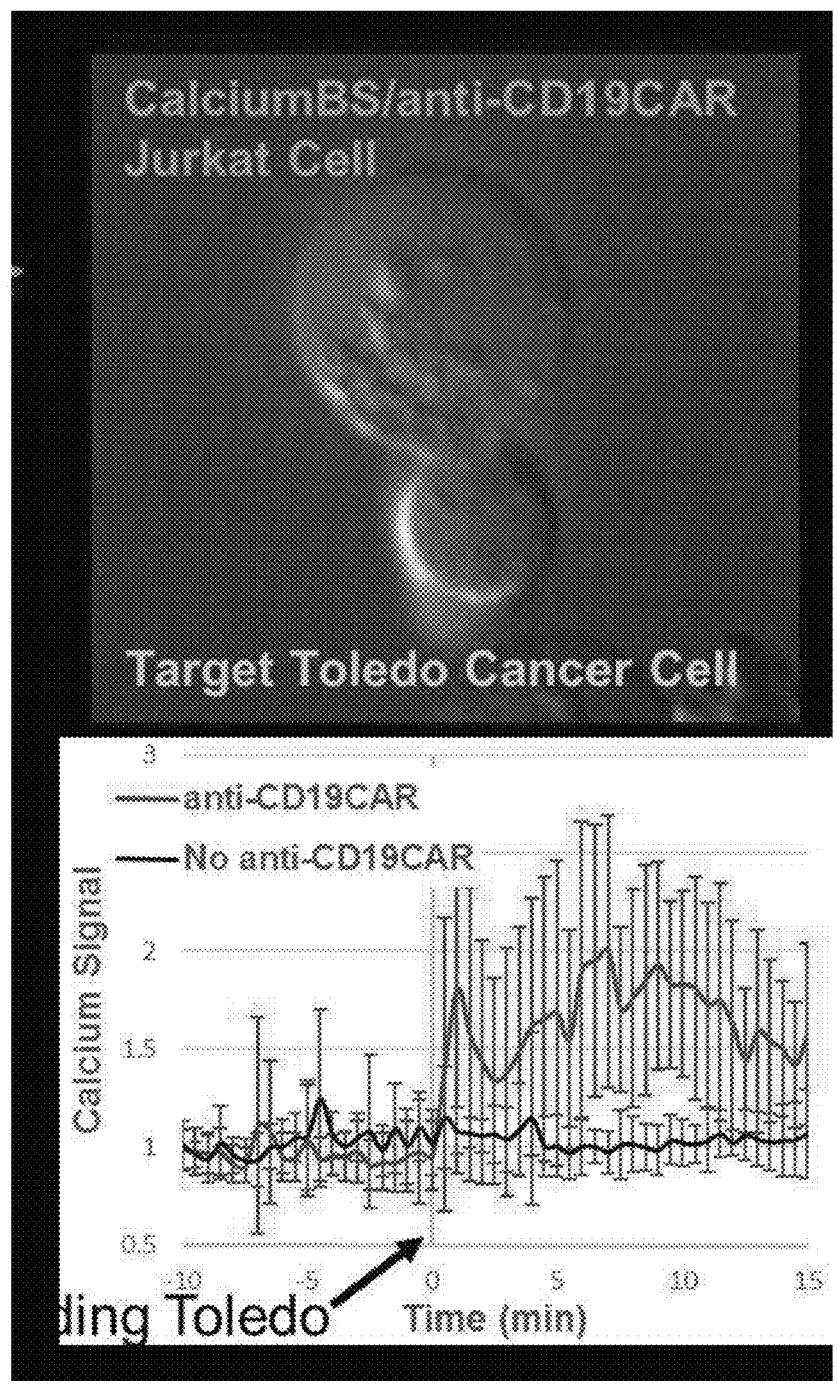
Figure 7C:
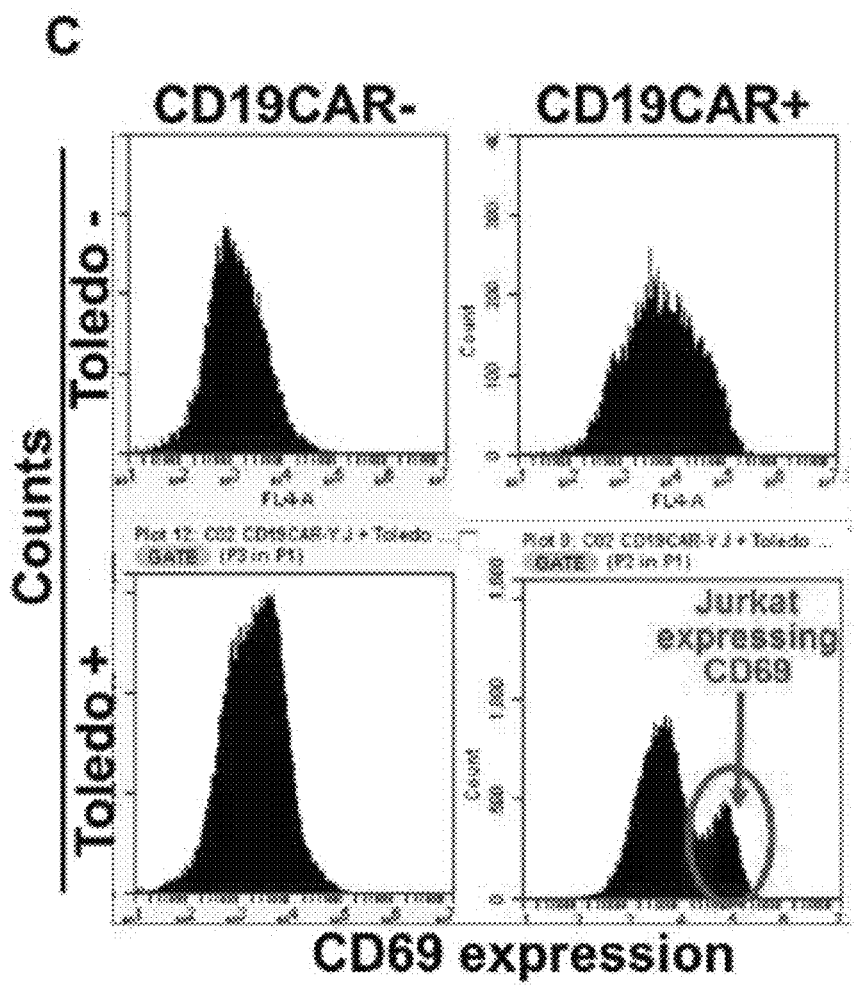

FIG. 7A-C schematically and graphically illustrate that biosensors can monitor and assess the functionality of CARs in Jurkat cells:

FIG. 7A schematically and graphically illustrates data showing that, after integrating CD19CAR into Jurkat T cells, CD19CAR-expressing Jurkats have a higher binding capacity toward the ligand CD19-expressing B cell lymphoma tumor cell line (Toledo), as comparing to Jurkats expressing the headless CD19CAR in which the extracellular domain of CD19CAR is truncated.

FIG. 7B schematically and graphically illustrates data showing a clear activation of calcium signaling as visualized by the calcium biosensors when Toledo cells are mixed with Jurkat cells expressing CD19CAR, but not those expressing the headless CD19CAR, data graphically presented in FIG. 7B, lower panel (arrow indicates time point that "Toledo cells" were added to the Jurkat cells expressing CD19CAR).

FIG. 7C graphically illustrates data from experiments that revealed that the expression of an activation marker CD69 in Jurkat cells expressing CD19CAR can be triggered by the engagement of Toledo cells.

The results from FIG. 7 confirm the functionality of CD19CAR in Jurkat cells, which can be monitored by biosensors.

For HEK293T cells, Targestar™-SA lipid microbubbles (Targeson, La Jolla, Calif.) ($1 \times 10^9$/mL) were mixed with biotinylated Arg-Gly-Asp (RGD) peptides (0.01 mg/mL) (Peptide International, Louisville, Ky.) for 20 min (36). Immediately after removing the culture media in the dish, 5 μl of the microbubble-RGD mixture was added into the dish. The dish was then flipped upside down for 5 min to allow microbubbles to float up and attach to the cell membrane. For Jurkat cells and PBMCs, membrane proteins on the cell surface were biotinylated by EZ-Link™ Sulfo-NHS-Biotin (2 mM) (Thermo Scientific, Rockford, Ill.) for 15 min and washed with PBS before the cells were incubated with and coupled to Targestar™ microbubbles.

Figure 8A:
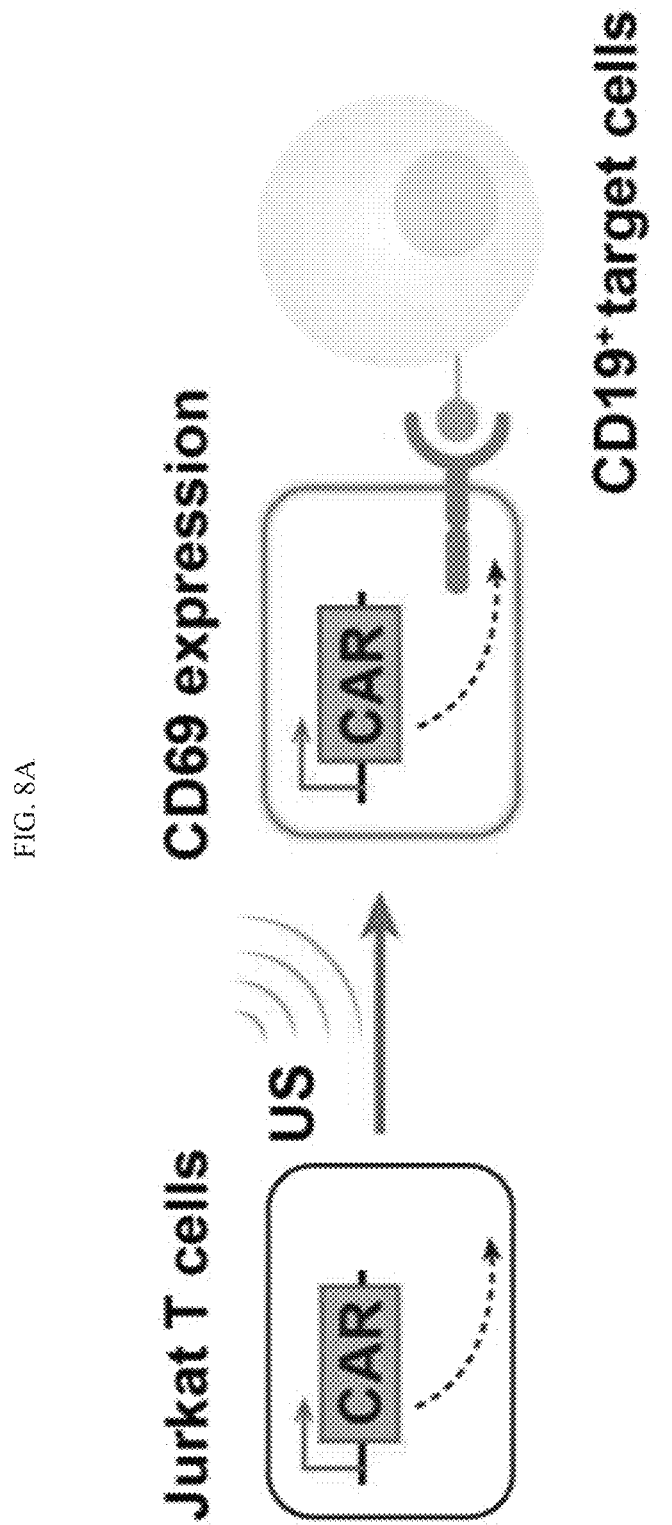
FIG. 8A-C schematically and graphically illustrate data showing that ultrasound can induce the gene expression and activation of Jurkat cells against target cancer cells.
Figure 8B:
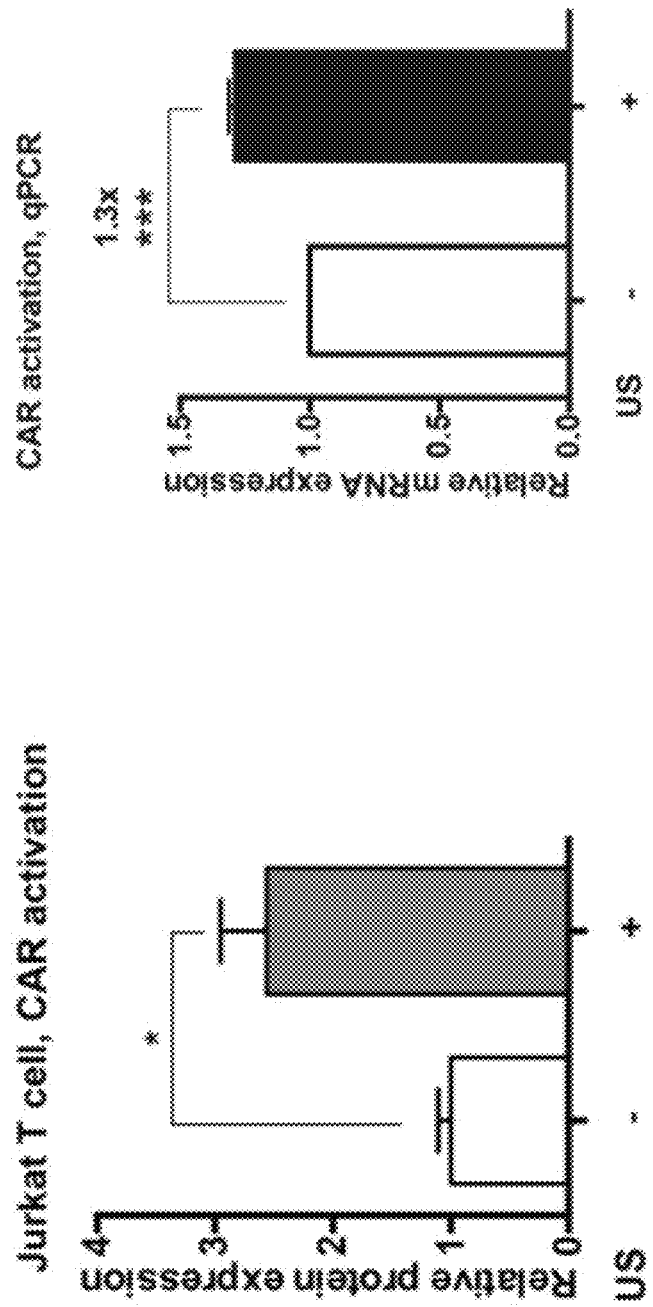
Figure 8C:
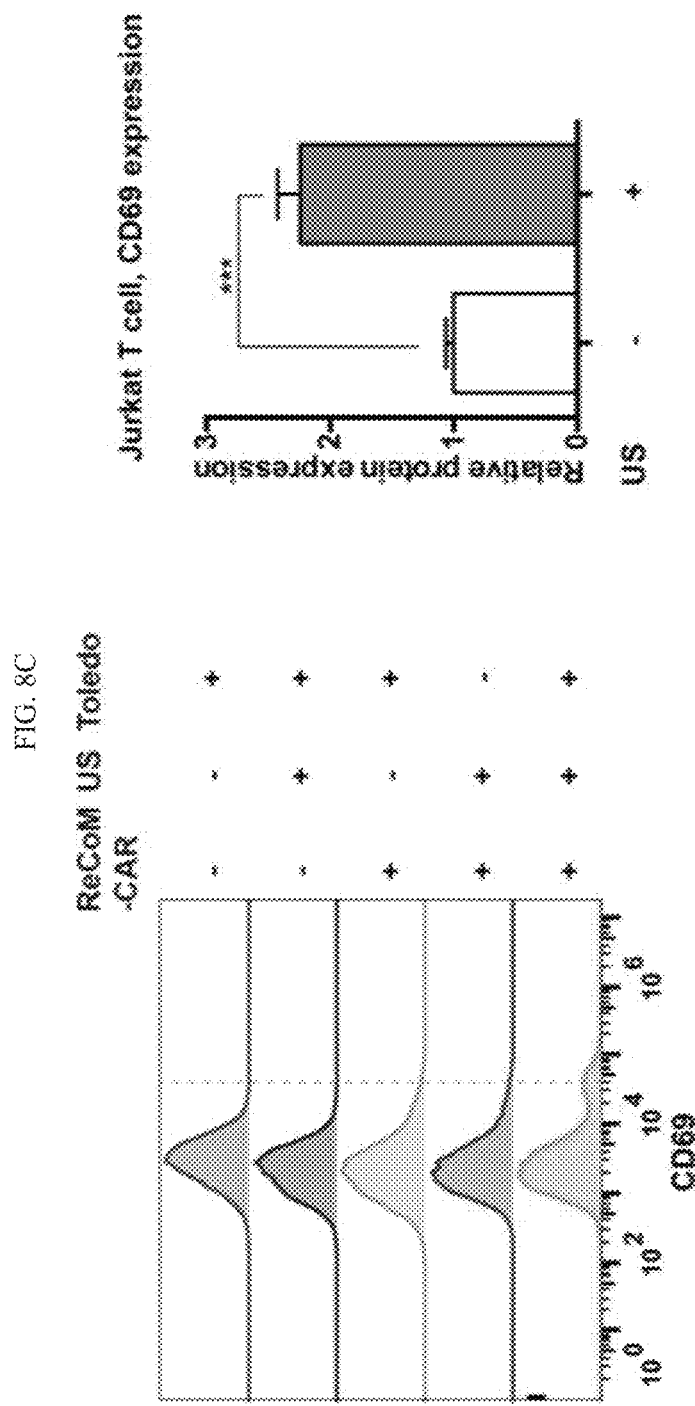

FIG. 8A-C schematically and graphically illustrate data showing that ultrasound can induce the gene expression and activation of Jurkat cells against target cancer cells:

FIG. 8A schematically illustrates a GTM containing NFAT promoter being introduced into Jurkat cells whose surfaces were then biotinylated and coupled to streptavidin-coated microbubbles; ultrasound stimulation can induce the CD19CAR expression in these Jurkats without additional exogenous Piezo1 or mechano-sensors, possibly because Jurkats express high levels of endogenous Piezo1 and other mechanosensitive channels (see, e.g., Pottosin, Delgado-Enciso et al. Biochim Biophys Acta. 2015 January; 1848(1 Pt A):51-9).

FIG. 8B graphically illustrates data showing that the production of CD19CAR in Jurkat cells can be stimulated by ultrasound to allow the engagement of Toledo cells, which leads to the expression of CD69 as an activation marker of Jurkats. These results demonstrate that GTMs can be engineered into Jurkats for the ultrasound-induced production of CARs which can mediate the immune-engagement with cancer cells to activate Jurkats.

FIG. 8C graphically illustrates data showing: Left panel, Representative histograms of T cell activation in Jurkat cells by quantifying the expression of cell surface protein marker CD69. Jurkat and Toledo mixtures were stained with Alexa647-conjugated anti-CD69 antibody and analyzed by flow cytometry; Right panel, The bar graphs represent CD69 up-regulation (normalized percentage of CD69 positive cells) in ultrasound-induced Jurkat cells upon Toledo cell engagement (n=8). Error bars indicate S.E.M., *p<0.05, ***p<0.001 from two-tailed Student t-test.

Figure 9:
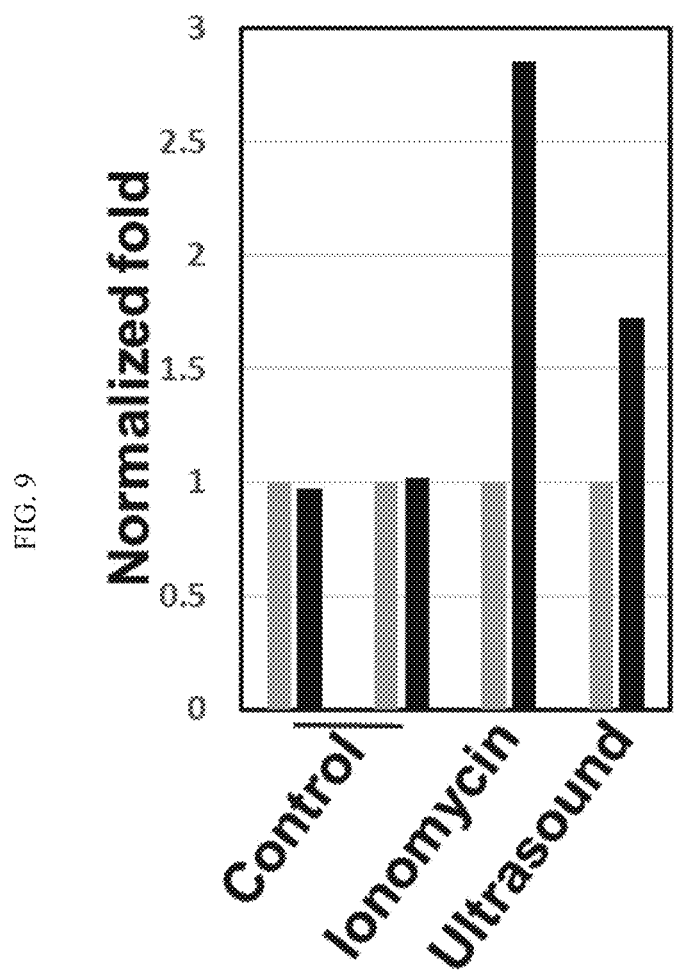
FIG. 9 graphically illustrates data showing that ultrasound induced gene expression, in particular, GFP reporter gene expression, in peripheral blood mononuclear cells (PBMCs), as further discussed, below.

FIG. 9 graphically illustrates data showing that ultrasound induced gene expression in PBMCs. We introduced a GTM containing the NFAT promoter in lentiviral vector into PBMCs to enable the induction of the GFP reporter gene expression in PBMCs upon ultrasound stimulation. This result provides the proof of concept that PBMCs can be engineered to sense ultrasound for the remote control of gene expressions, potentially CAR production.

Integrating Heat-Sensitive Genetic Transducing Modules (GTMs) and Focused Ultrasound In alternative embodiments, provided are methods and compositions for remotely and locally activating engineered chimeric antigen receptor (CAR) T cells by integrating heat-sensitive genetic transducing modules (GTMs) and focused ultrasound for immunotherapy purposes.

In alternative embodiments, provided are methods and compositions comprising use of high-intensity focused ultrasound (HIFU), which can ablate tumor lesions non-invasively and locally in cancer therapy, e.g., prostate cancer, pancreatic cancer, and the like, by inducing local temperature elevation (above 60° C.) and the subsequent necrosis of tumor cells. In addition, HIFU has also been utilized to control transgene activation via a heat-inducible promoter.

In alternative embodiments, provided are methods and compositions comprising integration of HIFU and heat-sensitive channels and GTMs; methods and compositions as provided herein can remotely and non-invasively activate intracellular nucleic acids in vivo or ex vivo in e.g., CAR T cells, with precise spatial and temporal control. In alternative embodiments, provided are designed GTMs comprising genes or nucleic acids of interest (e.g., encoding a CAR, a single chain antibody, or a single-domain antibody (also known as sdAb or nanobody) or an antibody fragment consisting of a single monomeric variable antibody domain) driven by (operably linked to) a mammalian or a human promoter or transcriptional activator activated by increased temperature, e.g., operably linked to a heat shock protein (Hsp), e.g., a 70B Hsp, promoter that can be activated by heat shock at e.g., 43° C. (for the 70B Hsp). HIFU is applied to generate local heating around cells carrying the heat-sensitive channels and GTMs, and turn on gene expression.

In alternative embodiments, components of this embodiment comprise:

Genetic transducing modules (GTMs): the nucleic acid, e.g., genes, of interest driven by the heat shock promoter, which can lead to the expression of nucleic acids/genes of interest and optionally also the production of a protein of interest, e.g., a therapeutic molecule, upon ultrasound heating. In alternative embodiments, a protein-encoding nucleic acid of interest encodes anti-CD19 CAR.

High-intensity focused ultrasound (HIFU): delivers focused mechanical energy to induce local thermal effect. The heat generated at the target location can activate cells with designed GTMs and induce the desired gene expression.

Cells: Human Embryonic Kidney (HEK) 293 cells, immortalized human T cell line Jurkat cells and peripheral blood mononuclear cells (PBMCs) containing the designed GTMs are used at different stages to test the feasibility and efficacy of embodiments as provided herein.

Exemplary method: the designed GTMs are introduced into the target cells, e.g., T cells, and (2) HIFU is applied to generate heat at the region around the target cells. Upon ultrasound induced heat shock, the cells containing the heat-sensitive GTMs are activated and start to express nucleic acids/genes of interest, e.g., a CAR-expressing nucleic acid, which has therapeutic effects including the triggering of T cell activation and killing of tumor cells.

Provided herein for the first time that HIFU is applied to activate nucleic acid in cells in vivo, including activating CAR expression in T cells by thermal effect in immunotherapy. This exemplary acoustic-thermogenetic systems provided herein is non-invasive and activates the engineered cells, e.g., immune cells, e.g., CAR T cells, remotely with deep penetration and millimeter-level spatial precision.

Figure 10:
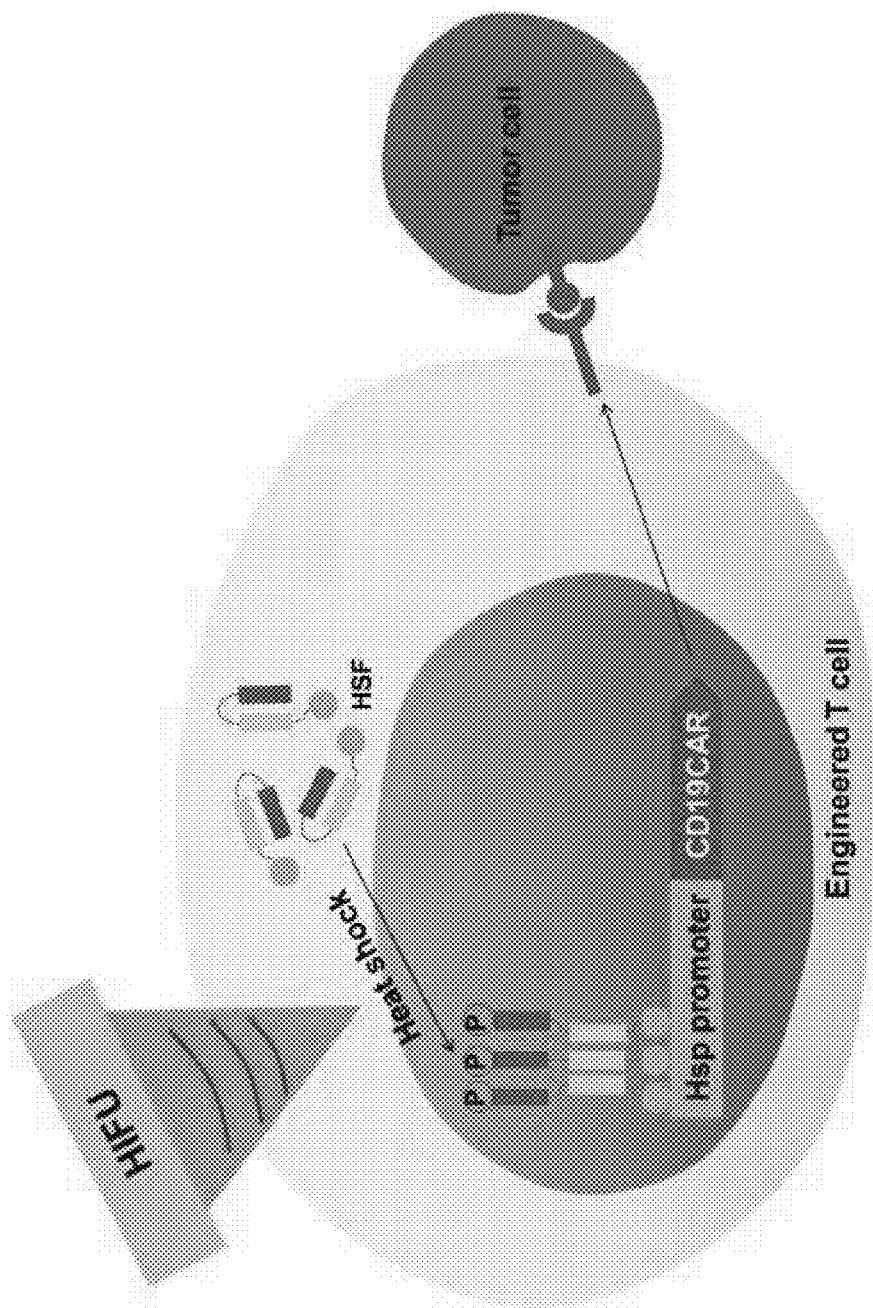
FIG. 10 schematically illustrates the remote activation of the production of biologically active molecules (anti-CD19 CAR) by ultrasound-induced heat shock, as further discussed, below.

FIG. 10 schematically illustrates the remote activation of the production of biologically active molecules (anti-CD19 CAR) by ultrasound-induced heat shock. The T cell is engineered to carry the GTM consisting of the Hsp promoter and the anti-CD19 CAR. HIFU is applied to generate heat at the location of the engineered T cells. Upon ultrasound-induced heat shock, the heat shock factor (HSF) monomers in the cytoplasm form homotrimers and translocate into the nucleus, where they bind to the Hsp promoter and activate downstream gene expression. The biologically active anti-CD19 CAR is then synthesized and expressed on the cell surface, where it recognizes the CD19 antigen expressed on the surface of tumor cells and triggers the killing of the tumor cells.

HEK Cells Transfected with the GTMs can be Activated by Heat Shock

Figure 11:
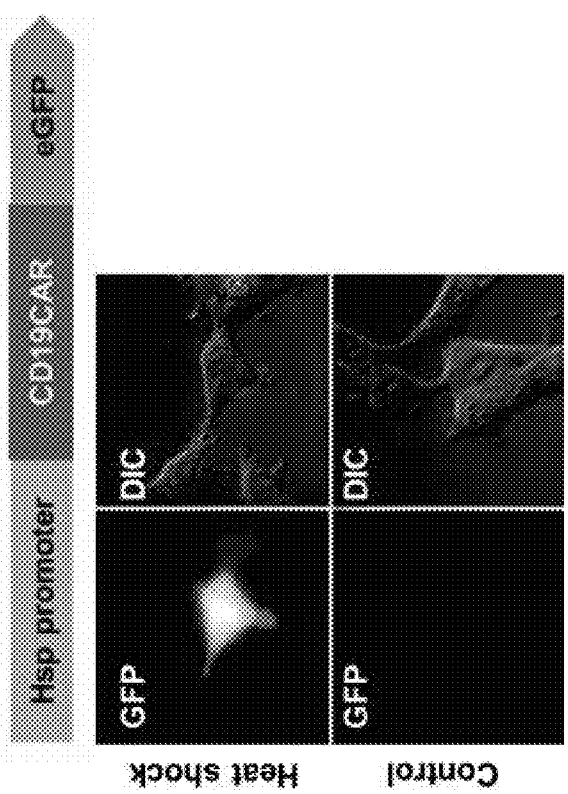
FIG. 11A-B schematically and in images illustrates heat induced gene expression in HEK cells.
Figure 11:
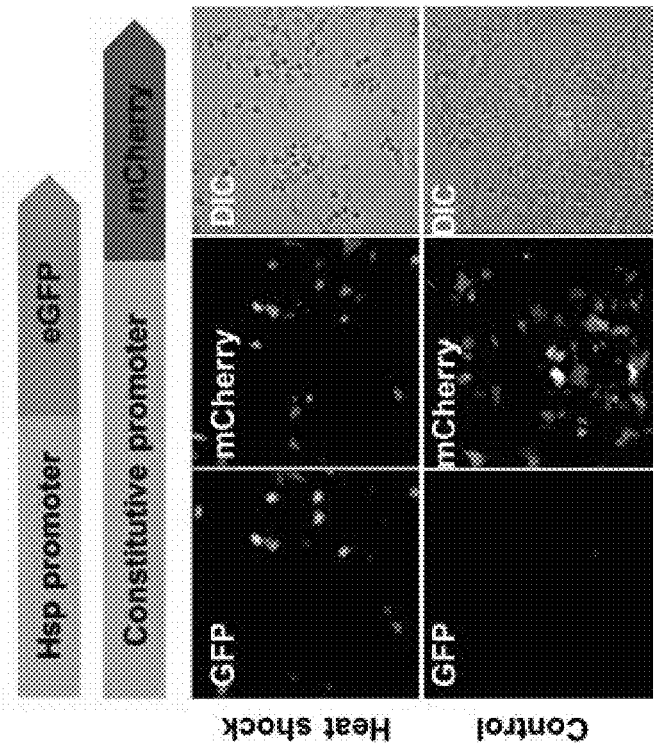

Human Embryonic Kidney (HEK) cells were co-transfected with the heat-sensitive GTM (Hsp promoter driving the reporter eGFP) and a constitutively expressed mCherry. The heat shock stimulation was applied by incubating cells in a 43° C. incubator for 60 min and then transferring to a 37° C. incubator for another 8 hr to 24 hr, while the control cells were maintained at 37° C. during the whole period. The heat shock caused a clear induction of eGFP expression in HEK cells bearing the heat-sensitive GTM (FIG. 11A). Similarly, we tested another heat-sensitive GTM composed of eGFP tagged anti-CD19 CAR driven by the Hsp promoter with the same settings. Again, heat shock successfully induced eGFP expression in HEK cells transfected with this GTM (FIG. 11B). These results demonstrate the feasibility of activating target gene expression by heat shock in HEK cells.

FIG. 11A-B schematically and in images illustrates heat induced gene expression in HEK cells:

FIG. 11A upper panel schematically illustrates an exemplary GTM design where an Hsp promoter driving the reporter eGFP was used as the heat-sensitive GTM with a constitutively expressing mCherry serving as a normalization reference to minimize cell-cell heterogeneity; and the images on the lower panels show the heat-induced gene expression of the GTM; (Left panels): the reporter gene expression in heat shock or control groups; (middle panels): the constitutive reference mCherry expression; (right panels): DIC images of the cells.

FIG. 11B upper panel illustrates an exemplary GTM containing an Hsp promoter driving the anti-CD19 CAR and the reporter eGFP; the images on the lower panels show the heat-induced gene expression of the GTM; (Left panels): the reporter gene expression in heat shock or control groups; (right panels): DIC images of the cells.

Figure 12:
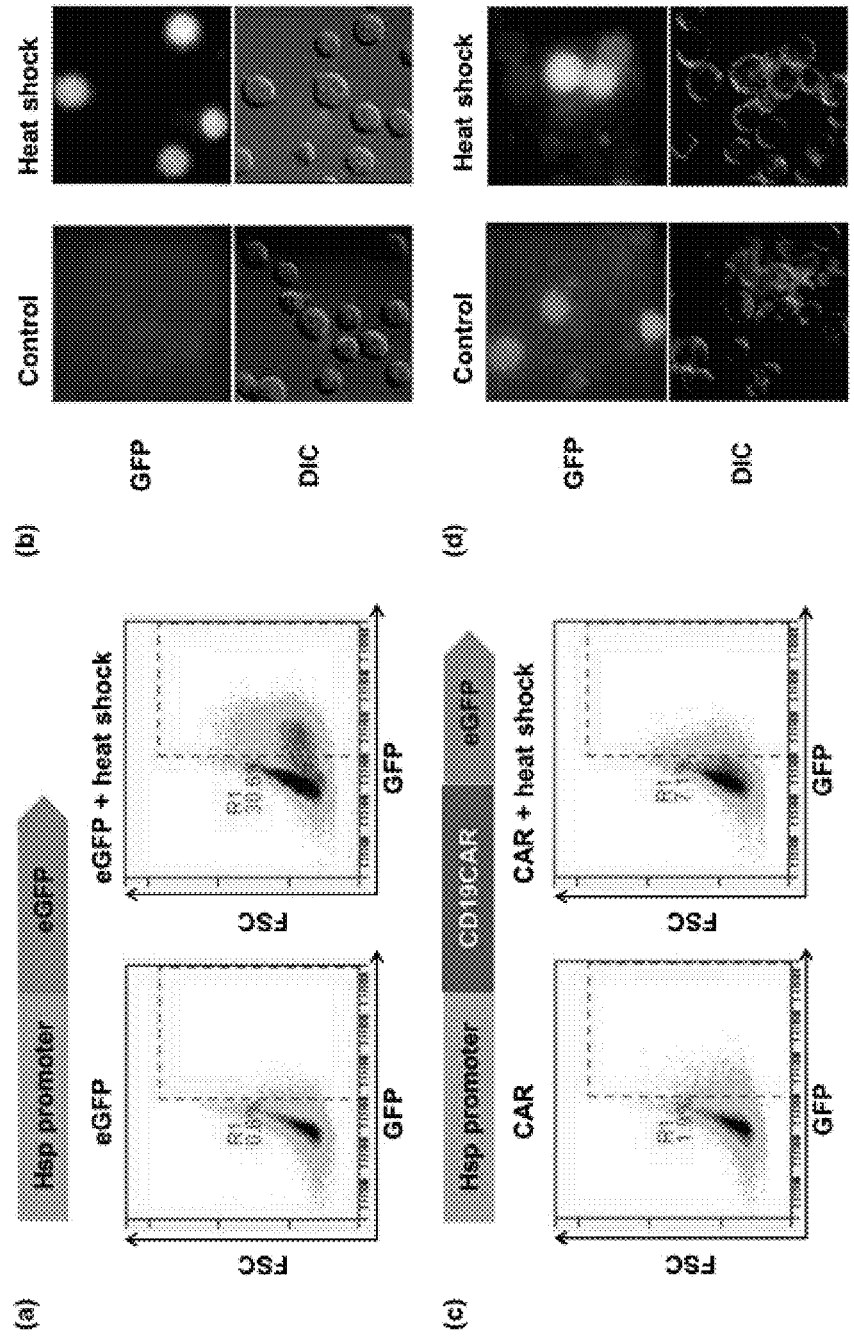
FIG. 12A-D schematically and graphically illustrate the expression of genes of interest in Jurkat T cells carrying the designed GTMs after heat shock induction: the dashed (red) box R1 in A and C represents the gated area where the cells are counted as positively expressing the reporter gene.

Jurkat Cells Carrying the GTMs can Express Genes of Interest Upon Heat Shock Activation To further test the heat-induced gene activation in T cells, we delivered the designed GTMs into Jurkat cells, an immortalized human T cell line, by either lentiviral infection (FIG. 11) or electroporation (FIG. 12). The engineered Jurkat cells were then heat shocked by incubating in a 43° C. incubator for 60 min, with the control group kept at 37° C. all the time.

For Jurkat cells transfected with the GTM containing the Hsp promoter driven eGFP, the percentage of the cells expressing eGFP increased from 0.8% to 30.6% 13 hr after heat shock as compared to the control (FIG. 12A). Similarly, the GTM containing the eGFP-tagged anti-CD19 CAR driven by the Hsp promoter was also introduced to Jurkat cells. A 2.5-fold increase (from 1.9% to 7.1%) in eGFP expression level was observed in the heat shocked group comparing to the control (FIG. 12B-C). These results indicate that Jurkat T cells containing the heat-sensitive GTMs can be induced to express the genes of interest upon heat shock.

FIG. 12A-D schematically and graphically illustrate the expression of genes of interest in Jurkat T cells carrying the designed GTMs after heat shock induction:

FIG. 12A graphically illustrates representative flow cytometry data showing the expression of eGFP in Jurkat cells transduced with the Hsp promoter driven eGFP 13 hr after heat shock; Left panels: control group; Right panels: heat shock group.

FIG. 12B schematically illustrate representative images showing the expression of eGFP 18 hr after heat shock in Jurkat cells transduced with the GTM in FIG. 12A.

FIG. 12C graphically illustrates representative flow cytometry data of Jurkat cells expressing the eGFP tagged anti-CD19 CAR driven by the Hsp promoter 13 hr after heat shock; Left panel: control group; Right panel: heat shock group.

FIG. 12D schematically illustrate representative images showing the expression of eGFP 23 hr after heat shock in Jurkat cells transduced with the GTM in FIG. 12C.

The Expressed Anti-CD19 CAR Induced by Heat Shock is Capable of Triggering Jurkat T Cell Activation CD69 is a cell surface marker that is increasingly expressed on T cell surface after its activation. To examine the function of the heat-induced anti-CD19 CAR, the Jurkat cells carrying the Hsp promoter driven CD19CAR GTM 12 hr after heat shock were mixed with Toledo cells (B cells expressing CD19 antigen). Upon mixing, the anti-CD19 CAR expressed on the surface of the heat shocked Jurkat cells would interact with the CD19 antigen expressed on the surface of Toledo cells, triggering Jurkat cell activation and the increased expression of CD69.

Figure 13:
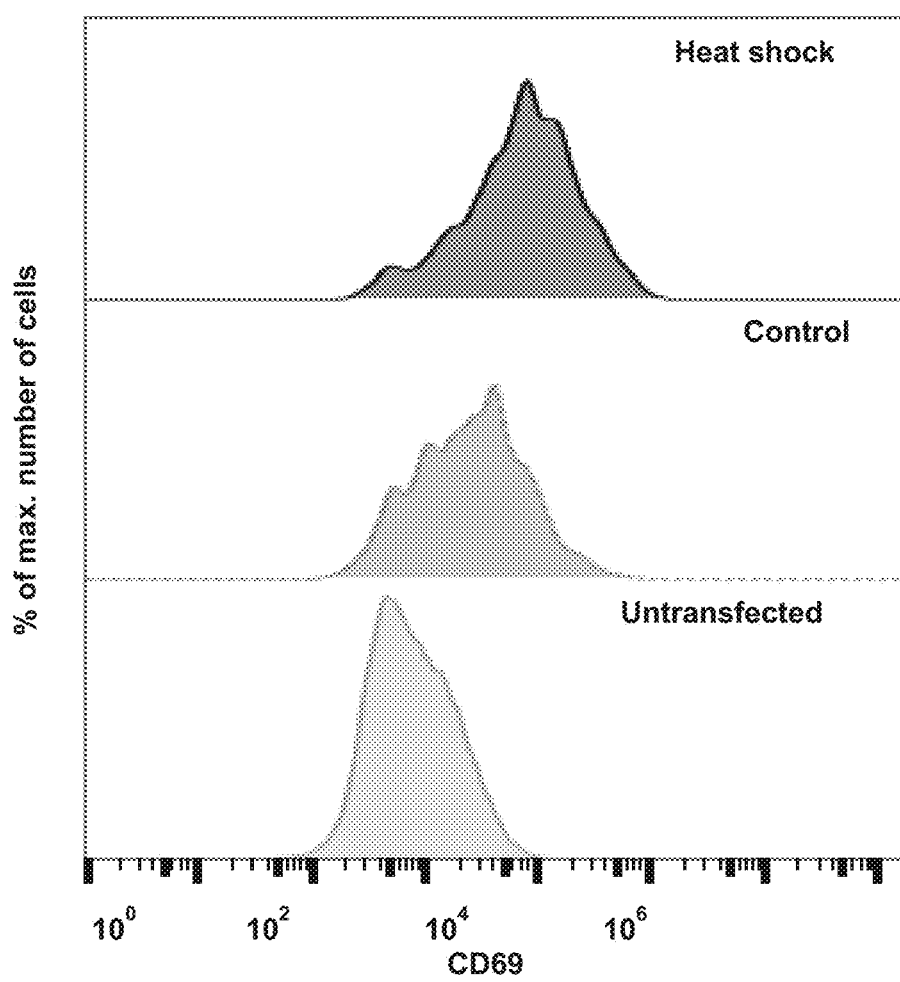
FIG. 13 graphically illustrates data showing CD69 expression as an indicator of Jurkat activation upon interacting with Toledo cells: CD69 expression was measured in untransfected Jurkats (lower panel), Jurkats hosting a GTM with (upper panel) or without (middle panel) heat shock, as further discussed, below.

Indeed, as illustrated in FIG. 13, the CD69 expression level 24 hr after mixing increased in the heat shocked Jurkat cells as compared to the control groups, either Jurkats hosting GTMs kept at 37° C. during the whole period of experiment (control) or Jurkats not transfected with GTMs but mixed with Toledo cells (untransfected). These results suggest that the expressed anti-CD19 CAR induced by heat shock is biologically functional in activating the signaling cascades of Jurkats upon the engagement with target tumor cells.

FIG. 13 graphically illustrates data showing CD69 expression as an indicator of Jurkat activation upon interacting with Toledo cells: CD69 expression was measured in untransfected Jurkats (lower panel), Jurkats hosting a GTM with (upper panel) or without (middle panel) heat shock. This GTM is composed of an Hsp promoter, an anti-CD19 CAR and eGFP. The Jurkat cells 12 hr after heat shock stimulation were mixed with Toledo cells. CD69 staining was performed after another 24 hr using a fluorophore-conjugated anti-CD69 antibody and analyzed by flow cytometry. In all cases, heat shock was conducted by incubating the cells in 43° C. incubator for 60 min, while the control group was incubated at 37° C.

The Heat-Sensitive GTMs can be Induced in Primary Human T Cells

Since Jurkat cells lack killing capacity, we will employ primary human T cells for examining the therapeutic effects of the heat-inducible CAR. As a first step, we tested the Hsp promoter mediated gene activation in response to heat shock stimulation in primary human T cells. The heat-sensitive GTM containing the Hsp-driven eGFP fused with the PGK-driven mCherry) was introduced into primary human T cells by lentiviral infection. Heat shock (43° C. for 60 min) was then applied and induced eGFP expression in 97.8% of the successfully infected (mCherry+) cells, while merely 5.6% of those under the control condition (kept at 37° C.) showed eGFP expression (FIG. 14A). We further tested heat-induced gene activation in primary human T cells by transducing them with the GTM containing the heat-sensitive anti-CD19 CAR. We detected the surface expression of CD19CAR in 0.7% and 6.7% of the T cells (un-gated) by antibody staining in the control (37° C.) and heat shock (43° C. for 60 min) groups, respectively (FIG. 14B).

Figure 14:
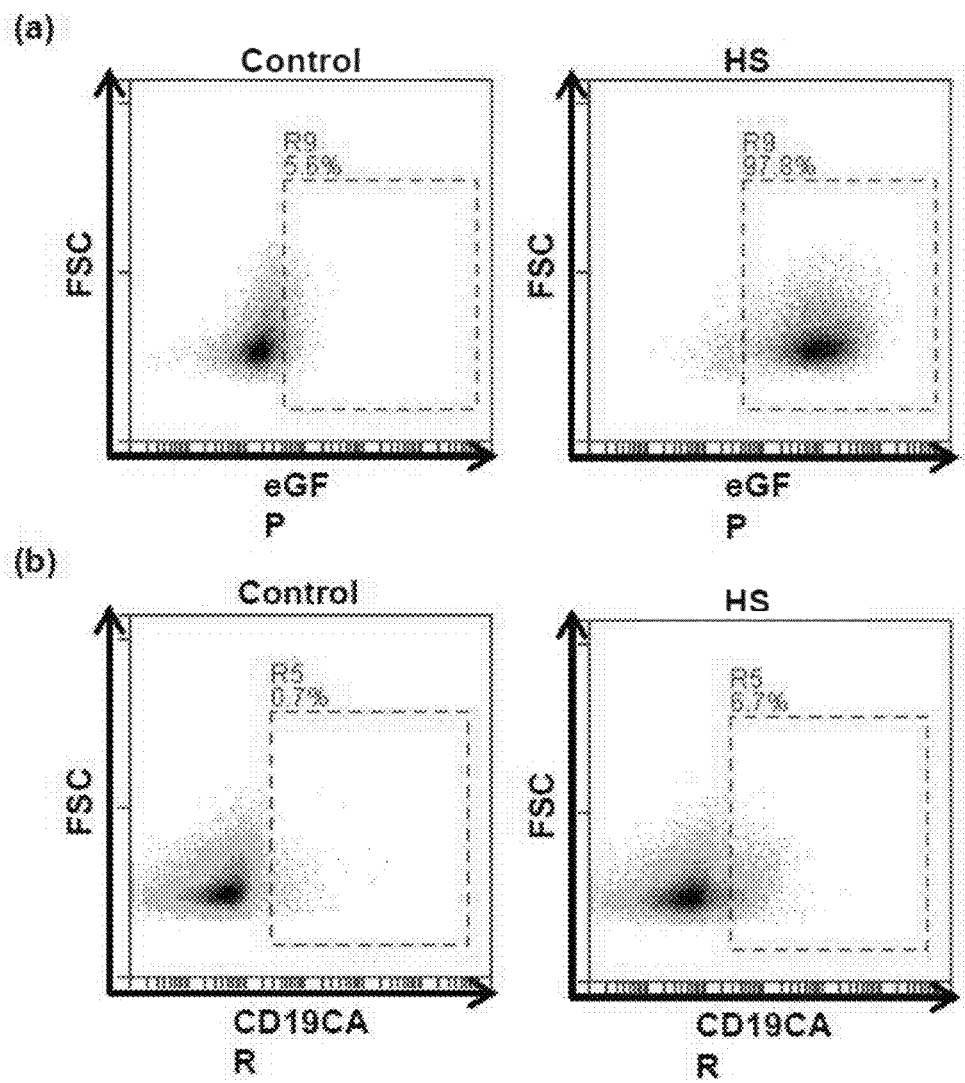
FIG. 14A-B graphically illustrate the exemplary heat-induced reporter eGFP and anti-CD19 CAR expression in primary human T cells: The dashed (red) box Rx represents the gated area where the cells are counted as positively expressing the reporter gene.

The results of FIG. 14 demonstrate the successful activation of the heat-sensitive GTMs in primary human T cells.

FIG. 14A-B graphically illustrate the exemplary heat-induced reporter eGFP and anti-CD19 CAR expression in primary human T cells:

FIG. 14A graphically illustrates representative flow cytometry data showing the percentage of eGFP-expressing cells in the gate of mCherry+ cells. Cells were lentivirally infected with the heat-sensitive GTM containing the Hsp-driven eGFP fused with the constitutive PGK promoter-driven mCherry.

FIG. 14B graphically illustrates representative flow cytometry data showing the percentage of CD19CAR-expressing cells in the gate of live cells. Cells were lentivirally infected with the heat-sensitive GTM containing the Hsp-driven CD19CAR and stained with CD19CAR antibody prior to flow cytometry. Control: kept at 37° C. HS: heat shock in a 43° C. incubator for 60 min. Flow cytometry analysis was performed 18 hr after heat shock.

Ultrasound Stimulation Generates Heat in 3D Tissue Structures

Figure 15:
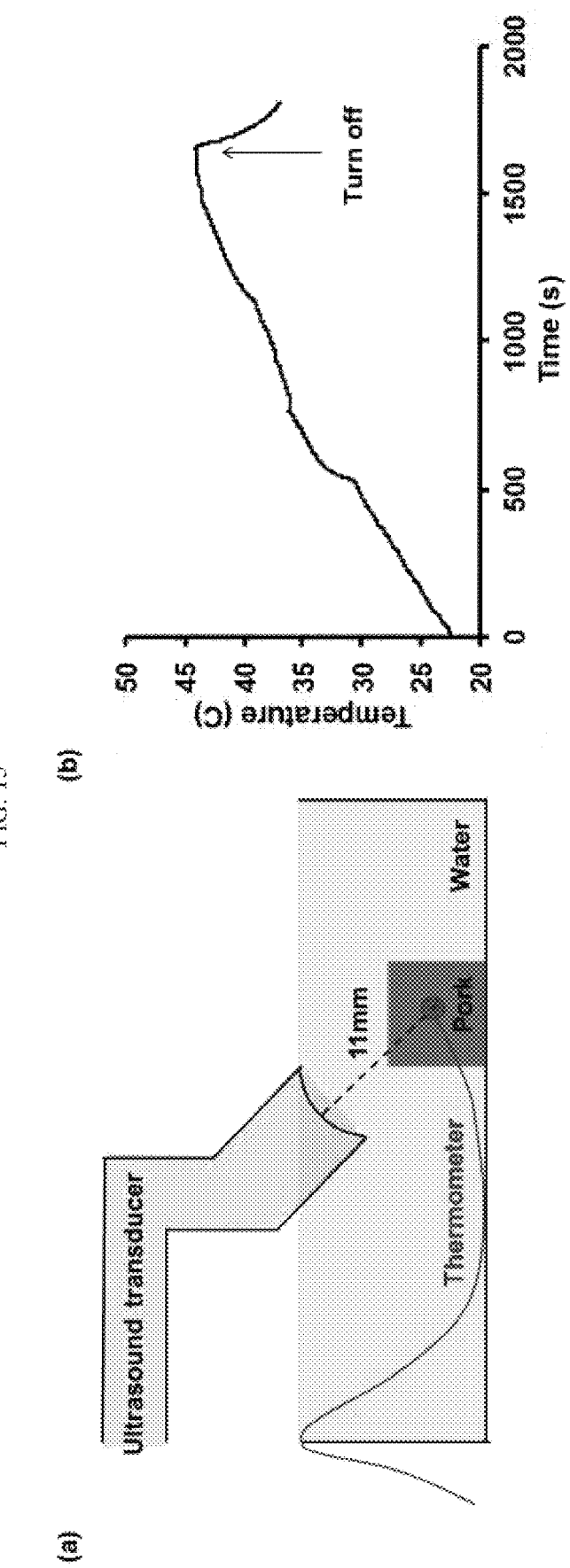
FIG. 15A-B schematically and graphically illustrate heat generation in pork tissues by HIFU.

We have built an in-house-designed focused ultrasound transducer with a focal length of 11 mm and external radius aperture of 8 mm. The diameter of the focal area is approximately 1 mm. Square waves with different parameters were tested for the performance in generating heat. We have demonstrated that this system can induce a controllable temperature increase to above 43° C. in raw pork tissues (FIG. 15).

FIG. 15A-B schematically and graphically illustrate heat generation in pork tissues by HIFU:

FIG. 15A schematically illustrates an ultrasound transducer, a half cubic inch piece of raw pork, and a thermocouple connected to a thermometer are immersed in water. The thermocouple is embedded close to the focal point of the ultrasound inside the pork. A square wave with 30% duty factor, 95 V peak-to-peak voltage $V_{pp}$ and 10 ms period was applied initially, with duty factor and $V_{pp}$ gradually tuned to 38% and 120 V during the experiment.

FIG. 15B graphically illustrates data showing the time course represents the temperature near the focal point measured by the embedded thermocouple in the pork.

Ultrasound Stimulation Activates Heat-Sensitive GTMs by Generating Heat

We designed a system composed of the abovementioned ultrasound transducer and cells transfected with heat-sensitive GTMs to examine the effect of ultrasound stimulation (see FIG. 6A). The Jurkat cells are maintained in complete RPMI medium in a cone-shaped polypropylene tube and sealed with paraffin film. The whole tube is submerged in and therefore fixed by agarose gel. A thermocouple connected to a digital thermometer is employed to measure the temperature of the gel right outside of the tube.

In a representative experiment, we applied a square ultrasound wave with moderate parameters (95 V $V_{pp}$, 30% duty factor and 10 ms period) to the cells for 60 min by focusing the transducer inside the cone-shaped tube. The temperature of the gel approximately 3 mm away from the focal point was measured to stabilize at 37.5° C.±1° C. within 10 min (see FIG. 6B). The temperature of the medium inside the tube was presumably higher by an order of degrees (around 43° C.) empirically.

Figure 16:
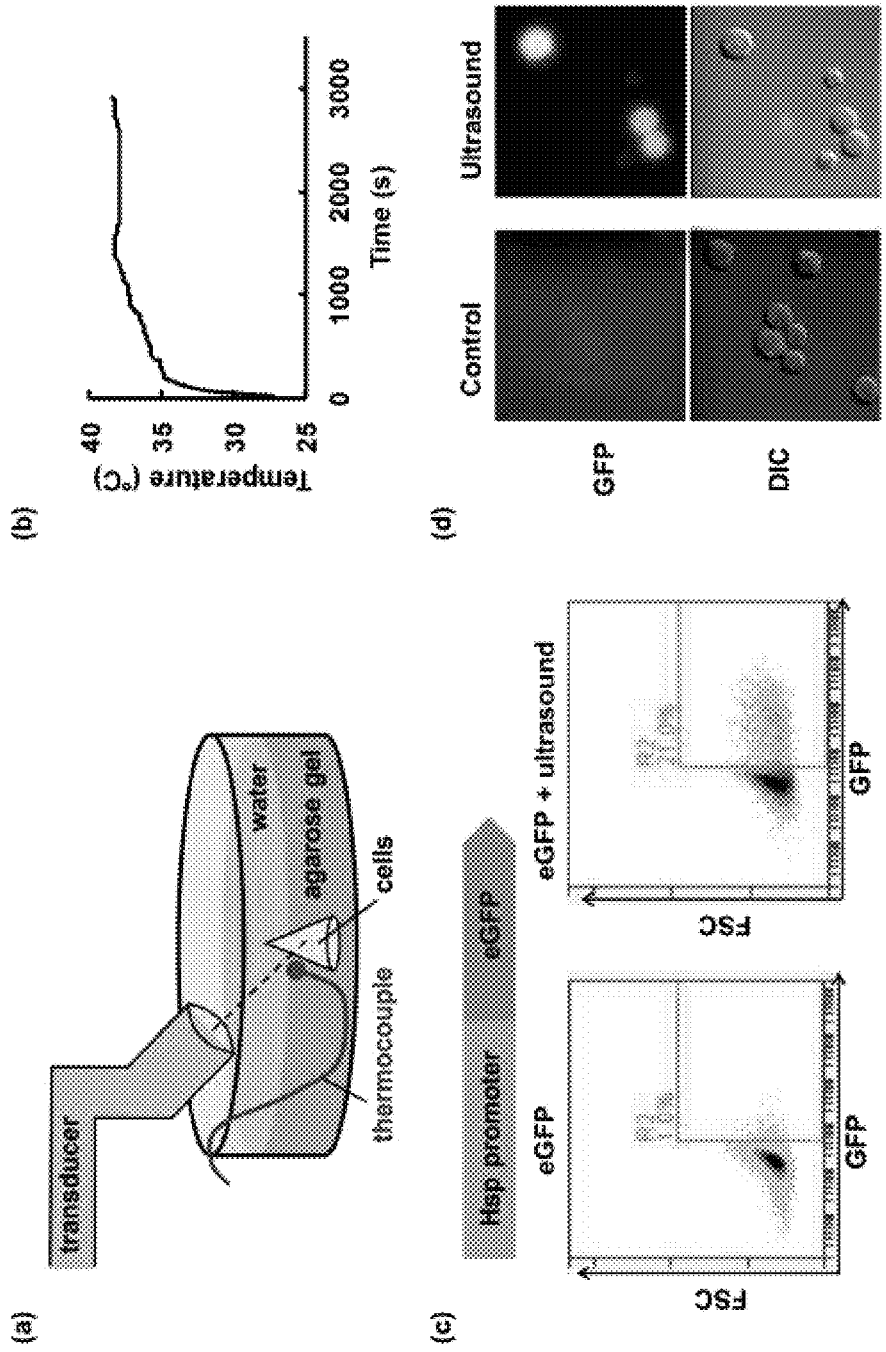
FIG. 16A-D schematically and graphically illustrate HIFU heating induced gene expression in Jurkat cells.

It was observed that the GFP expressing cell percentage was 21.0% in Jurkat containing the heat-sensitive GTM (Hsp promoter driving the reporter eGFP) 20 hr after ultrasound stimulation as compared to 1% in the control group (FIG. 16C-D). This result shows that the applied ultrasound stimulation indeed turned on the heat-sensitive GTM and induced target gene expression by generating heat shock on the cells. Although finer measurement and control of the ultrasound induced temperature increase will further improve the precision of our system, this proof-of-concept result demonstrates that ultrasound can be utilized to control gene expression in Jurkat T cells.

FIG. 16A-D schematically and graphically illustrate HIFU heating induced gene expression in Jurkat cells:

FIG. 16A schematically illustrates the experimental setup of the ultrasound stimulation system. Jurkat cells transfected with the heat-sensitive GTM (Hsp promoter driven eGFP) are maintained in a sealed cone-shaped tube fixed by agarose gel. The ultrasound square waves were focused inside the tube to apply heat shock to the cells for 60 min.

FIG. 16B graphically illustrates data showing the temperature of the gel right outside the tube (approximately 3 mm away from the focal point) measured by an embedded thermocouple during ultrasound stimulation.

FIG. 16C graphically illustrates flow cytometry data showing a drastic increase in eGFP expressing cells 20 hours (hr) after ultrasound induced heat shock in the ultrasound stimulated group as compared to the control.

FIG. 16D illustrates images of corresponding microscope images of FIG. 16C: Left panels, eGFP images of the reporter gene; Right panels, DIC images of the Jurkat cells.

FIG. 17A-D schematically and graphically illustrate data showing that ultrasound can induce the CD19 CAR expression and activation of PBMC cells against target cancer cells:

FIG. 17A schematically illustrates that a GTM containing NFAT promoter was introduced into Jurkat cells whose surfaces were then biotinylated and coupled to streptavidin-coated microbubbles.

FIG. 17B graphically illustrates data showing that ultrasound stimulation can induce calcium signaling.

FIG. 17B graphically illustrates data showing CD19CAR expression in these PBMCs without additional exogenous Piezo1 or mechano-sensors.

FIG. 17D graphically illustrates data showing the production of CD19CAR in PBMC cells can be stimulated by ultrasound to allow the engagement of Nalm6 cells, which leads to the killing effect on target tumor cells.

Figure 17:
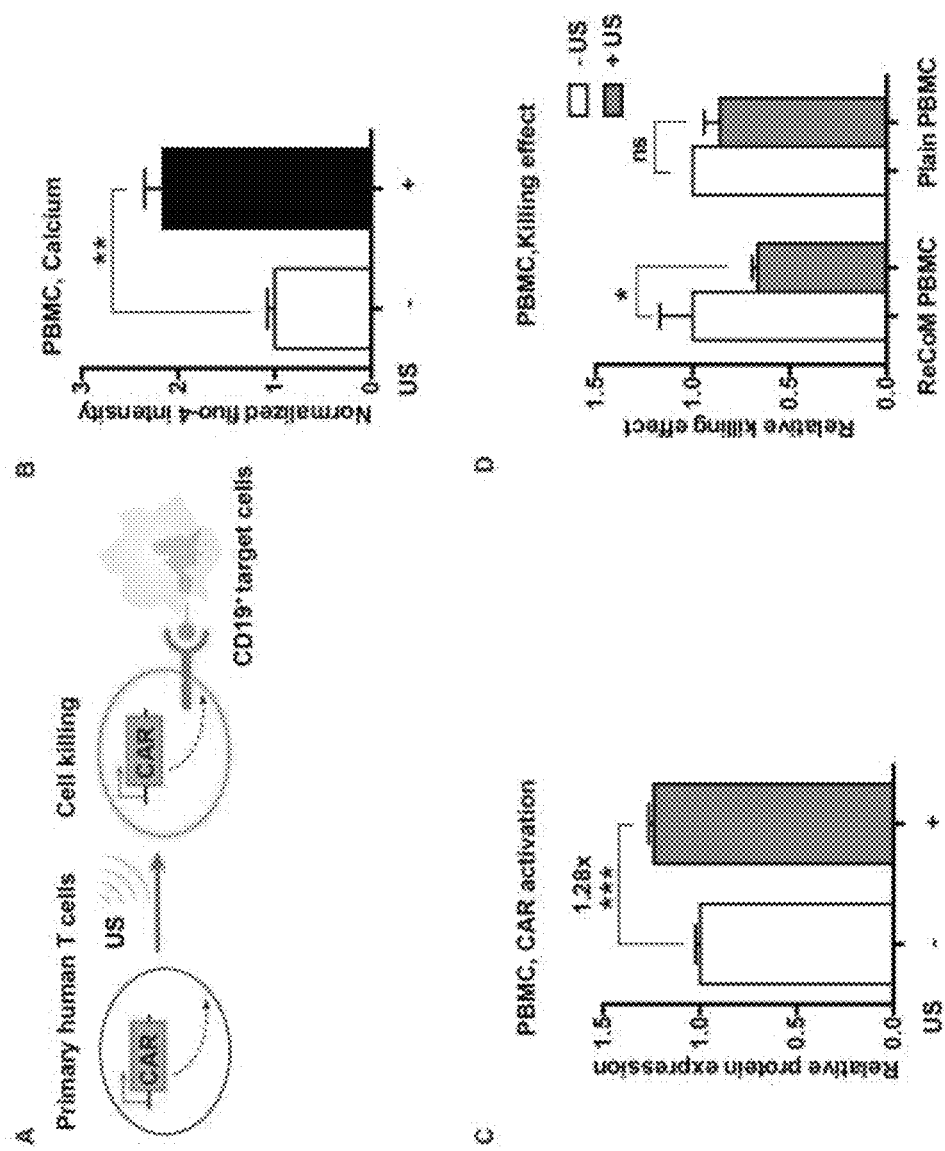
FIG. 17A-D schematically and graphically illustrate data showing that ultrasound can induce the CD19 CAR expression and activation of PBMC cells against target cancer cells.

The results of FIG. 17 demonstrate that GTMs can be engineered into PBMCs for the ultrasound-induced production of CARs which can mediate the immune-engagement and killing of the cancer cells.

Developing Cre-Lox Recombination-Based Heat-Sensitive GTMs

The current heat-sensitive GTMs utilize the Hsp promoter to directly drive the expression of target genes such as the CD19CAR. As a result, the heat-induced CD19CAR molecules undergo degradation after removal of the heat stimulus, potentially decreasing the potency of the heat-inducible CAR-T cells. To convert this transient expression to a permanent one, we developed a new set of heat-sensitive GTMs incorporating the Cre-Lox recombination system.

FIG. 18A schematically illustrates that the Cre recombinase is under the control of the Hsp promoter, while the target reporter gene is downstream of two Lox sites flanking a stop codon under the control of a constitutive promoter. Upon heat stimulation, the heat-activated Cre will act on the two Lox sites to cause recombination, leading to the removal of the stop codon and the constitutive expression of the reporter gene (e.g., CD19CAR).

FIG. 18B graphically illustrates data where this design was tested in Jurkat cells with CD19CAR as the reporter gene, and the expression level of CD19CAR was quantified under various heat simulation durations.

FIG. 18C graphically illustrates data showing that CD19CAR expression in 21.3% and 26.8% of the unsorted cells with 15 min and 30 min heat shock, respectively, significantly higher than the 11.5% in the control cells cultured at 37° C.

Figure 18:
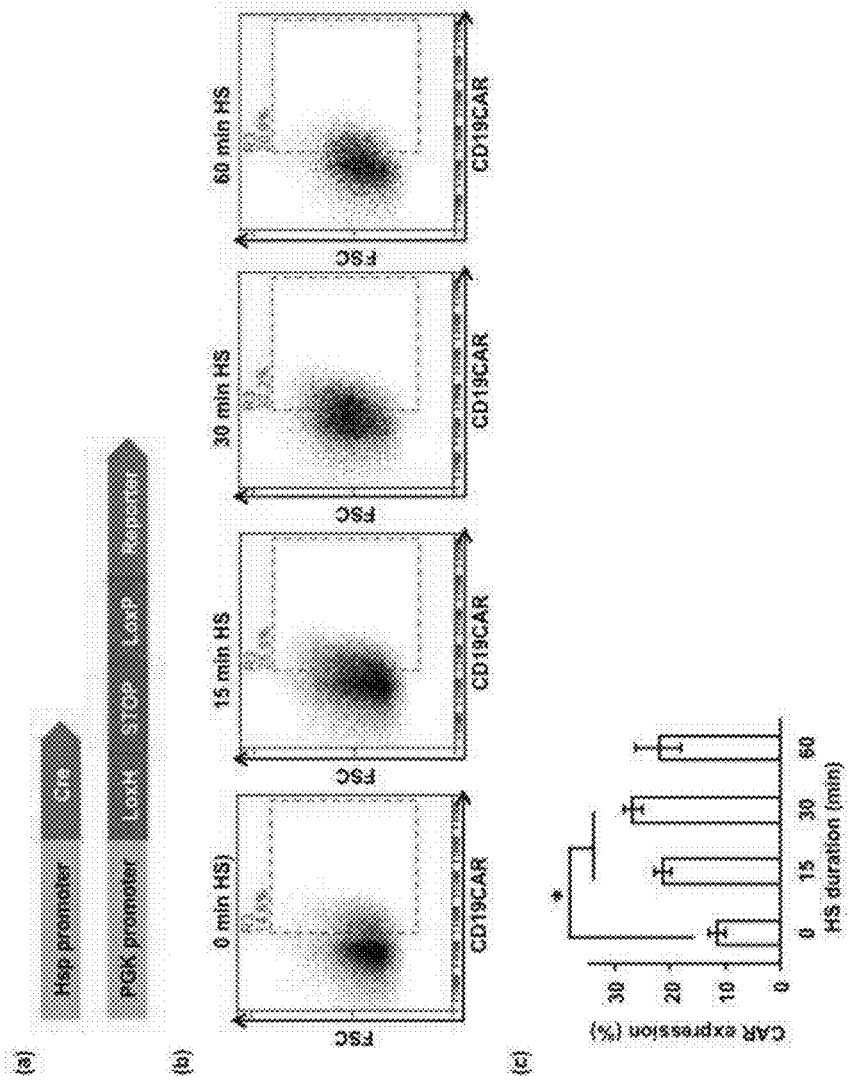
FIG. 18A schematically illustrates that the Cre recombinase is under the control of the Hsp promoter, while the target reporter gene is downstream of two Lox sites flanking a stop codon under the control of a constitutive promoter, as further discussed, below.
FIG. 18B graphically illustrates data where this design was tested in Jurkat cells with CD19CAR as the reporter gene, and the expression level of CD19CAR was quantified under various heat simulation durations; the dashed (red) box R3 in B represents the gated area where the cells are counted as positively expressing the reporter gene.
FIG. 18C graphically illustrates data showing that CD19CAR expression (expressed in percent, %) in 21.3% and 26.8% of the unsorted cells with 15 min and 30 min heat shock ("HS duration", in minutes (min)), respectively, significantly higher than the 11.5% in the control cells cultured at 37° C.; the symbol * represents a statistical significance among the groups compared with p<0.05.

The results of FIG. 18 demonstrate that heat can activate the novel heat-sensitive GTMs integrating the Cre-Lox system.

In alternative embodiments, any method known in the art can be used to implant into a cell or transfect a cell in vivo or ex vivo with a nucleic acid construct used to practice embodiments as provided herein. In alternative embodiments, cells are transfected with or have inserted therein a nucleic acid construct used to practice embodiments as provided herein ex vivo, and the cell is then implanted in or into a tissue or organ, or is administered to or implanted in an individual in need of treatment. For example, a nucleic acid construct used to practice embodiments as provided herein can be delivered by intramuscular (IM) injection, by intravenous (IV) injection, by subcutaneous injection, by inhalation, by a biolistic particle delivery system (e.g., a so-called "gene gun"), and the like, e.g., as an outpatient, e.g., during an office visit. In alternative embodiments, this "peripheral" mode of delivery, e.g., expression vehicles, vectors, recombinant viruses and the like injected IM or IV, can circumvent problems encountered when genes or nucleic acids are expressed directly in an organ, for example, in brain, liver, skeletal muscle, lung or kidney cells or in any tissue.

For example, in alternative embodiments a recombinant virus (e.g., a long-term virus or viral vector), or a vector, or an expression vector, and the like containing within and able to express a nucleic acid construct used to practice embodiments as provided herein, can be injected, e.g., in a systemic vein (e.g., IV), or by intramuscular (IM) injection, by inhalation, or by a biolistic particle delivery system (e.g., a so-called "gene gun"), e.g., as an outpatient, e.g., in a physician's office.

In alternative embodiments, days or weeks later (e.g., four weeks later), the individual, patient or subject is administered (e.g., inhales, is injected or swallows), a chemical or pharmaceutical that induces expression of the nucleic acid construct used to practice embodiments as provided herein; for example, an oral antibiotic (e.g., doxycycline or rapamycin) is administered once daily (or more or less often), which will activate the expression of the gene. In alternative embodiments, after the "activation", or inducement of expression (e.g., by an inducible promoter) of the nucleic acid construct used to practice embodiments as provided herein, the desired protein expressed. When the physician or subject desires discontinuation of the treatment, the subject simply stops taking the activating chemical or pharmaceutical, e.g., antibiotic.

In alternative embodiments, methods as provided herein comprise use of nucleic acid (e.g., gene or polypeptide encoding nucleic acid) delivery systems to deliver a payload of a nucleic acid construct used to practice embodiments as provided herein to a cell or cells in vitro, ex vivo, or in vivo, e.g., as gene therapy delivery vehicles. In alternative embodiments, expression vehicle, vector, recombinant virus, or equivalents used to practice methods as provided herein are or comprise: an adeno-associated virus (AAV), a lentiviral vector or an adenovirus vector; an AAV serotype AAV5, AAV6, AAV8 or AAV9; a rhesus-derived AAV, or the rhesus-derived AAV AAVrh.10hCLN2; an organ-tropic AAV; and/or an AAV capsid mutant or AAV hybrid serotype. In alternative embodiments, the AAV is engineered to increase efficiency in targeting a specific cell type that is non-permissive to a wild type (wt) AAV and/or to improve efficacy in infecting only a cell type of interest. In alternative embodiments, the hybrid AAV is retargeted or engineered as a hybrid serotype by one or more modifications comprising: 1) a transcapsidation, 2) adsorption of a bi-specific antibody to a capsid surface, 3) engineering a mosaic capsid, and/or 4) engineering a chimeric capsid. It is well known in the art how to engineer an adeno-associated virus (AAV) capsid in order to increase efficiency in targeting specific cell types that are non-permissive to wild type (wt) viruses and to improve efficacy in infecting only the cell type of interest; see e.g., Wu et al., Mol. Ther. 2006 September; 14(3):316-27. Epub 2006 Jul. 7; Choi, et al., Curr. Gene Ther, 2005 June; 5(3):299-310. For example, the rhesus-derived AAV AAVrh.10hCLN2 or equivalents thereof can be used, wherein the rhesus-derived AAV may not be inhibited by any pre-existing immunity in a human; see e.g., Sondhi, et al., Hum Gene Ther. Methods. 2012 October; 23(5):324-35, Epub 2012 Nov. 6; Sondhi, et al., Hum Gene Ther. Methods. 2012 Oct. 17; teaching that direct administration of AAVrh.10hCLN2 to the CNS of rats and non-human primates at doses scalable to humans has an acceptable safety profile and mediates significant payload expression in the CNS.

In alternative embodiments, all recombinant DNA techniques are carried out according to standard protocols, for example, as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Microbubble Fabrication and Applications

In alternative embodiments, any method for making microbubbles can be used to practice embodiments as provided herein, and produces microbubbles of various size and consistency. Variables include shell material, size, dispersion, biological properties, drug properties, and drug loading capacity. A few exemplary fabrication methods are detailed below:

Mechanical Agitation

This exemplary method is a two-step process to create phospholipid-shelled microbubbles. First, the phospholipids are created from conventional methods such as thin phospholipid film hydration, phase inversion, or ethanol injection. Ideally, the drugs of interested are incorporated into the phospholipids before MB formation. The liposomal dispersion is placed into vials with the remaining headspace filled with the gas to be captured within the microbubbles. The vials are then agitated at several thousand oscillations per minute. Drug loading after formation requires incubation of the drug and microbubbles. This method is versatile and gentle on fragile drug substances and targeting ligands. Important considerations for microbubble formation via mechanical agitation include agitation time, proportion of vial head-space to liquid volume, viscosity of the liposomal dispersion or micro-emulsion, temperature during agitation, and concentration of drug and phospholipids.

Emulsification

This exemplary method creates oil-in-water (O/W) emulsions as a means of encapsulating lipophilic drugs. The inner layer is typically an organic solvent. These can be created by freeze-drying an emulsion of a lyophilizable water-immiscible organic solvent and subsequently removing the aqueous and organic phases. This leaves the emulsion matrix in the frozen vial which is then filled with the microbubble core gas. The lipophilic drugs are incorporated into the inner layer during the organic emulsion phase. The microbubble will immediately form in the injected gas. To improve biocompatibility, hydrophilic biomaterials are sometimes included in the aqueous emulsion phase to coat the microspheres. This exemplary method can also be used to create double phase W/O/W emulsions for including lipophilic payloads, e.g., drugs. Important considerations for the emulsification method include: control of microbubble size (regulated by high-pressure extrusion), molecular weight of the polymeric shell material, and the amount of shell material to regulated shell thickness.

Probe-Type Sonication

This exemplary method can create microbubbles with denatured protein or phospholipid shells. Probe-type sonication uses low frequency ultrasound (US) at high intensity in an aqueous solution of microbubble core gas and shell material to disperse the gas. During this procedure the cavitation creates chemically reactive free-radicals and causes high temperatures (up to 808° C.) that denature the protein shell material and create stable covalent cross-bridging of protein thiol groups. This process creates stable shells with a high affinity for DNA and a wide range of drug molecules. Because of the high chemical and thermal stresses in making the microbubbles, therapeutic drugs are usually only loaded on the surface of preformed bubbles by drug incubation.

Spray-Drying

This exemplary method can be used to produce polymer, protein, or phospholipid shelled microbubbles. A liquid or slurry can be rapidly dried with a hot gas into a dry powder with a consistent particle size. To form pores or cavities in the particles, one can use a volatile ammonium salt or enclose volatile organic liquids into the spray-dry medium. As the solvent evaporates, the droplets shrink isotropically and the shell-material accumulates at the liquid-water interface. The outer shell material solidifies and the remaining solvent evaporates leaving a bubble. It is unclear whether the cavities are of uniform size or if there are multiple small voids in each bubble. Payloads can be volume-loaded into the shell by mixing with the shell material before microbubble formation. Compared to probe-type sonication, this method is quite gentle and provides a dry, stable product.

Flow-Focusing

This exemplary method can create microbubbles for e.g., flow focusing. To create these bubbles a core gas and the shell material are sent through a fine nozzle into a water bath. Microfluidic dual hydrodynamic focusing can be used to create monodispersed droplets. The droplets can have a gas core, inner oil shell layer, and outer phospholipid layer. The oil allows for uniform loading in high concentrations of hydrophobic and toxic drugs. Ligands can also be uniformly attached to the outer shell in the fabrication process.

Applications

In alternative embodiments, a microbubble, or a plurality of microbubbles, are provided, wherein the microbubbles are capable of responding to ultrasound or equivalent, and the microbubbles are linked or attached to at least one, or two or more, proteins, small molecules or moieties capable of specifically binding to the mechanoresponsive protein on the extracellular surface of the cell, such that energy generated by ultrasound stimulation of the ultrasound-responsive microbubble. In one embodiment, when microbubbles activate the mechanoresponsive protein this causes the mechanoresponsive protein to transmit or generate an intracellular response or signal, wherein optionally the intracellular response or signal comprises a calcium influx into the cell.

In alternative embodiments, microbubbles are mixed with cells, e.g., immune cells, ex vivo, which are then together administered in vivo, e.g., administrated intravenously or directly to a site of interest, e.g., to a tumor or an injury site. In alternative embodiments, microbubbles coated with streptavidin are mixed with surface biotinylated cells, e.g., immune cells, before administration. In alternative embodiments, microbubbles coated with streptavidin are mixed with biotinylated peptides or antibodies, e.g., RGD peptides.

In alternative embodiments, microbubbles are injected or otherwise delivered directly to or near a site of interest in vivo, e.g., to a tumor site, e.g., administered locally after introduction of cells of interest used to practice embodiments as provided herein, e.g., immune cells, into the body. In alternative embodiments, anywhere between $10^2$ to $10^{12}$ microbubbles are injected or otherwise delivered directly to or near a site of interest.

A number of embodiments of the invention have been described. Nevertheless, it can be understood that various modifications may be made without departing from the spirit and scope of the invention. Accordingly, other embodiments are within the scope of the following claims.

What is claimed is:

1. A method for remotely-controlling and non-invasively manipulating a nucleic acid expression in a cell, the method comprising:
(a) providing a cell or a plurality of cells:
  (i) expressing on the cell's extracellular surface a thermo- or mechanoresponsive protein; or
  (ii) comprising or having contained therein a nucleic acid or gene operably linked to a mammalian or a human promoter or transcriptional activator activated by increased temperature; or
  expressing on its extracellular surface the thermoresponsive or mechanoresponsive protein of (i) and comprising or having contained therein a nucleic acid or gene operably linked to a mammalian or a human promoter activated by increased temperature of (ii), and the nucleic acid is operably linked to:
    (1) a promoter or transcriptional activator responsive to an intracellular response or signal transmitted or generated by excitation of the mechanoresponsive protein by ultrasound stimulation of an ultrasound-responsive microbubble; or
    (2) a mammalian or a human promoter or transcriptional activator or thermoresponsive channel activated by increased temperature, optionally operably linked to a heat shock protein (Hsp),
  optionally a 70B Hsp, promoter that can be activated by heat shock, at optionally about 43° C. for the 70B Hsp; and
(b) stimulating the cell or plurality of cells with heat when the cell or plurality of cells comprises or has contained therein a nucleic acid or gene operably linked to a mammalian or a human promoter or transcriptional activator activated by increased temperature and/or ultrasound when the cell or plurality of cells expresses on its extracellular surface the mechanoresponsive protein,
either optionally generated by high-intensity focused ultrasound (HIFU), thereby: causing the thermo-response or mechanoresponsive protein to transmit or generate an intracellular response or signal to activate expression of the nucleic acid responsive the signal generated by excitation of the thermoresponsive or mechanoresponsive protein by ultrasound stimulation, and/or activating expression of the nucleic acid responsive the mammalian or a human promoter or transcriptional activator activated by increased temperature,
wherein when the cell or plurality of cells expresses on its extracellular surface a mechanoresponsive protein, providing an ultrasound-responsive microbubble, or a plurality of ultrasound-responsive microbubbles, capable of responding to ultrasound or equivalent, wherein the microbubble or the plurality of microbubbles are linked or attached to at least one, or two or more, proteins, small molecules or moieties capable of specifically binding to the mechanoresponsive protein on the extracellular surface of the cell or plurality of cells, such that energy generated by ultrasound stimulation of the ultrasound-responsive microbubble, or a plurality of ultrasound-responsive microbubbles is transmitted to the mechanoresponsive protein to activate the mechanoresponsive protein, wherein activation of the mechanoresponsive protein causes the mechanoresponsive protein to transmit or generate an intracellular response or signal, thereby remotely-controlling and non-invasively upregulating expression of the nucleic acid, thereby adding a new specificity, function or target cell to the cell or plurality of cells.

2. The method of claim 1, further comprising engineering into the cell or plurality of cells a vector or a Gene Transducing Module (GTM) such that upon stimulating the cell with:
  (a) ultrasound, thereby activating the thermoresponsive or mechanoresponsive protein, to transmit or generate an intracellular response or signal, and/or
  (b) heat,
the nucleic acid is expressed or is optimally expressed.

3. The method of claim 1, wherein the cell or plurality of cells is a human cell or a mammalian cell, or is a cell transplanted into a tissue, an organ, an organism or an individual, or is a non-human transgenic animal genetically engineered to contain and express the Gene Transducing Module (GTM) or vector,
  wherein the GTM or vector comprises an exogenous thermoresponsive or mechanoresponsive protein and/or an exogenous nucleic acid operably linked to a promoter or transcriptional activator responsive to:
    (i) an intracellular response or signal transmitted or generated by excitation of the mechanoresponsive protein by ultrasound stimulation of an ultrasound-responsive microbubble; and/or
    (ii) heat.

4. The method of claim 3, wherein the microbubble, or a plurality of microbubbles are connected to or caused to be operably connected to the mechanoresponsive protein by linkage or attachment directly or indirectly to at least one, or two or more, proteins, small molecules or moieties capable of specifically binding to the mechanoresponsive protein,
  and optionally the at least one, or two or more, proteins, small molecules or moieties comprise a streptavidin (optionally bound to the microbubble, or a plurality of microbubbles) bound to an antibody or peptide or an RGD peptide linked to a biotin,
  wherein the antibody specifically binds to the mechanoresponsive protein, or the RGD peptide specifically binds to an integrin, which by binding the RGD peptide transmits the ultrasound signal to the mechanoresponsive protein,
  or optionally the microbubble, or a plurality of microbubbles are linked to a protein or moiety capable of specifically binding to the mechanoresponsive protein.

5. The method of claim 1, wherein the cell is an immune cell, or a mammalian cell.

6. The method of claim 1, wherein the nucleic acid is an endogenous gene, or an exogenous nucleic acid.

7. The method of claim 6, wherein the exogenous nucleic acid comprises a nucleic acid encoding or expressing a recombinant or an artificial T cell receptor, an antibody, a single chain antibody, or a single-domain antibody or an antibody fragment consisting of a single monomeric variable antibody domain.

8. The method of claim 1, wherein the thermo- or mechanoresponsive protein comprises a MechanoSensitive channel (MS channel).

9. The method of claim 1, wherein the thermoresponsive or mechanoresponsive protein is an exogenous protein or an endogenous protein, or a recombinantly engineered thermoresponsive or mechanoresponsive protein.

10. The method of claim 1, wherein
  the intracellular response or signal comprises a calcium influx into the cell.

11. The method of claim 2, wherein the vector or Gene Transducing Module (GTM) contains therein or comprises the nucleic acid operably linked to a mammalian or a human promoter or transcriptional activator activated by increased temperature,
  optionally operably linked to a heat shock protein (Hsp) or a 70B Hsp.

12. The method of claim 2, wherein the vector or Gene Transducing Module (GTM) contains therein or comprises a thermoresponsive or mechanoresponsive protein-expression nucleic acid operably linked to an inducible or constitutive promoter.

13. The method of claim 5, wherein the immune cell is a T cell, a monocyte, a macrophage, a dendritic cell, or a natural killer cell.

14. The method of claim 1, wherein the nucleic acid or gene is operably linked to a heat shock protein (Hsp) promoter that can be activated by heat shock.

15. The method of claim 14, wherein the heat shock protein (Hsp) promoter comprises a 70B Hsp promoter.

16. The method of claim 1, wherein the exogenous nucleic acid comprises or is contained in a vector or expression cassette.

17. The method of claim 1, wherein the intracellular response or signal transmitted comprises an intracellular calcium influx.

18. The method of claim 2, wherein upon stimulating the cell with ultrasound a thermoresponsive or mechanoresponsive transmembrane protein or channel is activated to transmit or generate an intracellular response or signal.

19. The method of claim 2, wherein the heat is generated by high-intensity focused ultrasound (HIFU).

20. The method of claim 2, wherein the nucleic acid that is expressed or is optimally expressed encodes a protein.

21. The method of claim 20, wherein the protein affects cell physiology or function, or adds a new target specificity to the cell, or is expressed on the cell's surface, or is secreted from the cell.

22. The method of claim 20, wherein the protein comprises an antibody, a chimeric antigen receptor (CAR), a single chain antibody, or a single-domain antibody or sdAb or nanobody, or an antibody fragment consisting of a single monomeric variable antibody domain.

23. The method of claim 1, wherein expressing on the thermo- or mechanoresponsive protein is a thermo- or mechanoresponsive transmembrane protein or transmembrane channel.

24. The method of claim 1, wherein remotely-controlling and non-invasively upregulating expression of the nucleic acid adds a function to the cell, or manipulates a physiologic and/or a genetic process in the cell, or immune cell.

25. The method of claim 24, wherein when the upregulated nucleic acid is a nucleic acid expressing or encoding a chimeric antigen receptor (CAR), a single chain antibody, or a single-domain antibody or an antibody fragment consisting of a single monomeric variable antibody domain.

26. The method of claim 8, MechanoSensitive channel (MS channel) comprises a Piezo1 or MscL, or ThermoSensitive channel (TS channel) comprises a TRPV1 channel.

27. The method of claim 6, wherein the exogenous nucleic acid comprises or is contained in a vector or expression cassette.

28. A method for remotely-controlling and non-invasively manipulating a nucleic acid expression in a cell,
the method comprising:
(a) providing a mammalian cell:
  (i) expressing on the cell's extracellular surface a thermo- or mechanoresponsive protein, optionally a thermo- or mechanoresponsive transmembrane protein or channel; or
  (ii) comprising or having contained therein a nucleic acid or gene operably linked to a mammalian or a human promoter or transcriptional activator activated by increased temperature; or
  expressing on its extracellular surface the thermoresponsive or mechanoresponsive protein of (i) and comprising or having contained therein a nucleic acid or gene operably linked to a mammalian or a human promoter activated by increased temperature of (ii), and the nucleic acid is operably linked to:
  (1) a promoter or transcriptional activator responsive to an intracellular response or signal transmitted or generated by excitation of the mechanoresponsive protein by ultrasound stimulation of an ultrasound-responsive microbubble or a plurality of ultrasound-responsive microbubbles,
  wherein the ultrasound-responsive microbubble or the plurality of ultrasound-responsive microbubbles are connected to or caused to be operably connected to the mechanoresponsive protein by linkage or attachment directly or indirectly to at least one, or two or more, proteins, small molecules or moieties capable of specifically binding to the mechanoresponsive protein, or
  (2) a mammalian or a human promoter or transcriptional activator or thermoresponsive channel activated by increased temperature,
  wherein the cell is transplanted into a tissue, an organ, an organism or an individual, or is a non-human transgenic animal genetically engineered to contain and express the Gene Transducing Module (GTM) or vector; and
(b) stimulating the cell with heat when the cell comprises or has contained therein a nucleic acid or gene operably linked to a mammalian or a human promoter or transcriptional activator activated by increased temperature and/or ultrasound when the cell expresses on its extracellular surface a mechanoresponsive protein, either optionally generated by high-intensity focused ultrasound (HIFU), thereby: causing the thermoresponse or mechanoresponsive protein to transmit or generate an intracellular response or signal to activate expression of the nucleic acid responsive the signal generated by excitation of the thermoresponsive or mechanoresponsive protein by ultrasound stimulation, and/or activating expression of the nucleic acid responsive the mammalian or a human promoter or transcriptional activator activated by increased temperature,
thereby remotely-controlling and non-invasively upregulating expression of the nucleic acid,
thereby adding a new specificity, function or target cell to the mammalian cell.

29. The method of claim 28, wherein the mammalian or the human promoter or transcriptional activator or thermoresponsive channel activated by increased temperature is operably linked to a heat shock protein (Hsp).

30. The method of claim 28, wherein the heat shock protein (Hsp) is operably linked to a 70B Hsp, promoter that can be activated by heat shock, or can be activated by exposure to about 43° C.

31. The method of claim 28, wherein the GTM or vector comprises an exogenous thermoresponsive or mechanoresponsive protein and/or an exogenous nucleic acid operably linked to a promoter or transcriptional activator responsive to:
(i) an intracellular response or signal transmitted or generated by excitation of the mechanoresponsive protein by ultrasound stimulation of an ultrasound-responsive microbubble; and/or
(ii) heat.

32. The method of claim 25, wherein the at least one, or two or more, proteins, small molecules or moieties comprise a streptavidin bound to an antibody or a peptide linked to a biotin, wherein the antibody specifically binds to the mechanoresponsive protein.

33. The method of claim 32, wherein the at least one, or two or more, proteins, small molecules or moieties comprise a streptavidin bound to the microbubble, or the plurality of microbubbles bound to an antibody or peptide linked to a biotin.

34. The method of claim 32, wherein the peptide comprises an RGD peptide, and the RGD peptide specifically binds to an integrin, which by binding the RGD peptide transmits the ultrasound signal to the mechanoresponsive protein.

35. The method of claim 28, wherein the mammalian cell is an immune cell or a plurality of immune cells.

36. The method of claim 35, wherein the immune cell is a T cell, a monocyte, a macrophage, a dendritic cell, or a natural killer cell.

37. The method of claim 28, wherein the mammalian cell is a human cell.

* * * * *